(12) United States Patent
Allway et al.

(10) Patent No.: US 6,238,855 B1
(45) Date of Patent: May 29, 2001

(54) PHOTOGRAPHIC ELEMENT CONTAINING A DIR COUPLER

(75) Inventors: Philip A. Allway, Croxley Green; Christina M. Watts, Harrow Weald; Paul L. Stanley, Harrow, all of (GB)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 09/467,421

(22) Filed: Dec. 20, 1999

(30) Foreign Application Priority Data

Dec. 24, 1998 (GB) .................................... 9828438

(51) Int. Cl.$^7$ .................................... G03C 7/305

(52) U.S. Cl. .................. 430/544; 430/558; 430/505; 430/955; 430/957

(58) Field of Search ................... 430/505, 544, 430/955, 546, 558, 957

(56) References Cited

U.S. PATENT DOCUMENTS

| | | |
|---|---|---|
| 3,933,500 | 1/1976 | Shiba et al. . |
| 5,356,764 | 10/1994 | Szajewski et al. . |
| 5,958,662 * | 9/1999 | Merkel et al. .................. 430/544 |
| 5,989,798 * | 11/1999 | Merkel et al. .................. 430/544 |
| 6,043,016 * | 3/2000 | Merkel et al. .................. 430/557 |

FOREIGN PATENT DOCUMENTS

| | | |
|---|---|---|
| 867 763 | 9/1998 | (EP) . |
| 4278942 | 10/1992 | (JP) . |

* cited by examiner

*Primary Examiner*—Geraldine Letscher
*Assistant Examiner*—Amanda C. Walke
(74) *Attorney, Agent, or Firm*—Sarah Meeks Roberts

(57) ABSTRACT

A photographic element comprising a support bearing one or more silver halide emulsions at least one of which comprises at least 50% silver chloride in association with one or more image dye-forming couplers and one or more DI(A)R couplers of formulae I or II:

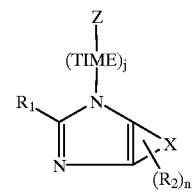

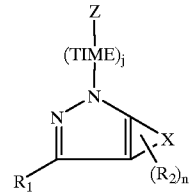

wherein:
  TIME is a timing group and
  $R_1$, $R_2$, Z, n, and j are as defined in the specification, wherein the DI(A)R coupler(s) in association with an emulsion comprising at least 50% silver chloride comprise at least about 25% to about 90% of the total amount of coupler in association with that emulsion and the total amount of coupler is the sum of the number of moles of image coupler(s) and the number of moles of the DI(A)R couplers in association with that emulsion.

20 Claims, 5 Drawing Sheets

PHOTOGRAPHIC ELEMENT CONTAINING A DIR COUPLER

FIELD OF THE INVENTION

The invention relates to photographic elements, such as colour negative films, and in particular to those which contain one or more aromatic bicyclic heterocycles containing an imidazole or pyrazole nucleus which can be used as coupling-off groups to give DIR couplers.

BACKGROUND OF THE INVENTION

Many silver halide photographic elements, in particular color negative films, contain so-called DIR (development inhibitor releasing) couplers. DIR couplers release inhibitors that can restrain silver development in the layer in which release occurs, as well as in other layers of a multilayer photographic material. DIR couplers can help control gamma (contrast), enhance sharpness (acutance), reduce granularity and provide color correction via interlayer inter-image effects. U.S. Pat. No. 3,933,500 broadly discloses DIR couplers with azole-type coupling off groups. EP-A-0 867 763 A describes purines and 1H-pyrazolo[3,4-d]pyrimidines as DIR couplers. A specific class of DIR couplers is DI(A)R couplers (development inhibitor anchiomeric-releasing) in which the release of the inhibitor is controlled by a timing mechanism.

It is desirable that DIR couplers efficiently reduce photographic contrast to provide benefits such as enhanced sharpness, reduced granularity and improved exposure latitude. It is also desirable that they give a reduction in the total amount of developed dye density ($D_{max}$).

U.S. Pat. No. 5,356,764 discloses the use of silver chloride emulsions in combination with DIRS incorporated at typically low levels with an image dye-forming coupler, e.g. the DIR comprises less than 8% of the total amount of coupler. EP 0 867 763A describes DIRs in an element containing silver chloride or silver bromoiodide at less than 11% of the total amount of coupler. JP-4278942 exemplifies silver iodide and silver bromoiodide-containing elements including DIRS at low percentage of total coupler, providing materials with good sharpness and superior shelf stability.

Silver chloride emulsions typically enable faster and easier processing, including faster and easier development, bleaching and fixing, combined with lower environmental impact.

PROBLEM TO BE SOLVED BY THE INVENTION

A problem, however, with such silver chloride emulsions is that proper development inhibition is much more difficult to achieve than with silver bromoiodide emulsions because of their superior developability. Thus there has been a need for a method of effectively reducing contrast and maximum amount of dye formed in elements containing silver chloride emulsions.

It has now been found that such inhibition of silver chloride emulsions can be achieved by incorporating the DI(A)R coupler at considerably higher than typical molar percentage of total amount of coupler.

SUMMARY OF THE INVENTION

According to the present invention there is provided a photographic element comprising a support bearing one or more silver halide emulsions, at least one of which comprises at least 50% silver chloride, in association with one or more image dye-forming couplers and one or more DI(A)R couplers of formulae I or II:

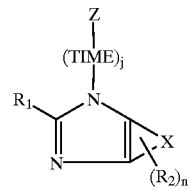

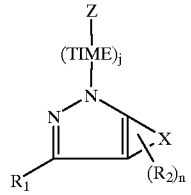

wherein:

Z is a moiety which can react with oxidized developer to release a coupling-off group;

$R_1$ is a hydrogen atom or a group selected from a halogen atom and an unsubstituted or substituted alkyl, aryl, alkoxy, aryloxy, alkyl- or aryl-thio, amino, alkyl- or aryl-amino, carbonamido, carbamoyl, alkoxy- or aryloxy-carbonyl, alkyl- or aryl-carbonyl, sulfonyl and sulfonamido group;

each of the $R_2$ substituents is a halogen atom or a group selected from an unsubstituted or substituted alkyl, aryl, alkoxy, aryloxy, alkyl- or aryl-thio, amino, alkyl- or aryl-amino, carbonamido, carbamoyl, alkoxy- or aryloxy-carbonyl, alkyl- or aryl-carbonyl, sulfonyl and sulfonamido group;

X represents the atoms required to make a second ring which is aromatic and contains at least one nitrogen atom;

n is from 0 to the number of carbon atoms in the second ring, with the proviso that if $R_1$ is hydrogen, n is at least 1;

TIME is a timing group and j is 0,1 or 2, wherein the DI(A)R coupler(s) in association with an emulsion comprising at least 50% silver chloride comprise at least about 25% to about 90% of the total amount of coupler in association with that emulsion and the total amount of coupler is the sum of the number of moles of image coupler(s) and the number of moles of the DI(A)R coupler(s) in association with that emulsion.

In another aspect of the invention there is provided a multicolour photographic element comprising a support bearing a cyan image-dye-forming unit comprising a red-sensitive silver halide emulsion layer and a cyan dye-forming coupler; a magenta image-dye-forming unit comprising at least one green-sensitive silver halide emulsion layer and a magenta dye-forming coupler; a yellow image-dye-forming unit comprising at least one blue-sensitive silver halide layer and a yellow dye-forming coupler, and associated therewith one or more DI(A)R couplers of formulae (I) or (II)

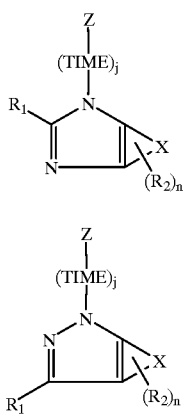

wherein:
- Z is a moiety which can react with oxidized developer to release a coupling-off group;
- $R_1$ is a hydrogen atom or a group selected from a halogen atom and an unsubstituted or substituted alkyl, aryl, alkoxy, aryloxy, alkyl- or aryl-thio, amino, alkyl- or aryl-amino, carbonamido, carbamoyl, alkoxy- or aryloxy-carbonyl, alkyl- or aryl-carbonyl, sulfonyl and sulfonamido group;
- each of the $R_2$ substituents is a halogen atom or a group selected from an unsubstituted or substituted alkyl, aryl, alkoxy, aryloxy, alkyl- or aryl-thio, amino, alkyl- or aryl-amino, carbonamido, carbamoyl, alkoxy- or aryloxy-carbonyl, alkyl- or aryl-carbonyl, sulfonyl and sulfonamido group;
- X represents the atoms required to make a second ring which is aromatic and contains at least one nitrogen atom;
- n is from 0 to the number of carbon atoms in the second ring, with the proviso that if $R_1$ is hydrogen, n is at least 1;
- TIME is a timing group and
- j is 0,1 or 2, wherein at least one of the layers comprises an emulsion comprising at least 50% silver chloride in association with one or more of the DI(A)R couplers, said DI(A)R couplers comprising at least about 25% to about 90% of the total amount of coupler in association with that layer, wherein the total amount of coupler is the sum of the number of moles of image coupler(s) and the number of moles of the DI(A)R couplers in association with that layer.

ADVANTAGEOUS EFFECT OF THE INVENTION

The DI(A)R couplers, when incorporated in elements of the invention, efficiently reduce development of silver chloride emulsions i.e. there is a reduction in both contrast and maximum amount of dye formed.

DETAILED DESCRIPTION OF THE INVENTION

Figure 1:
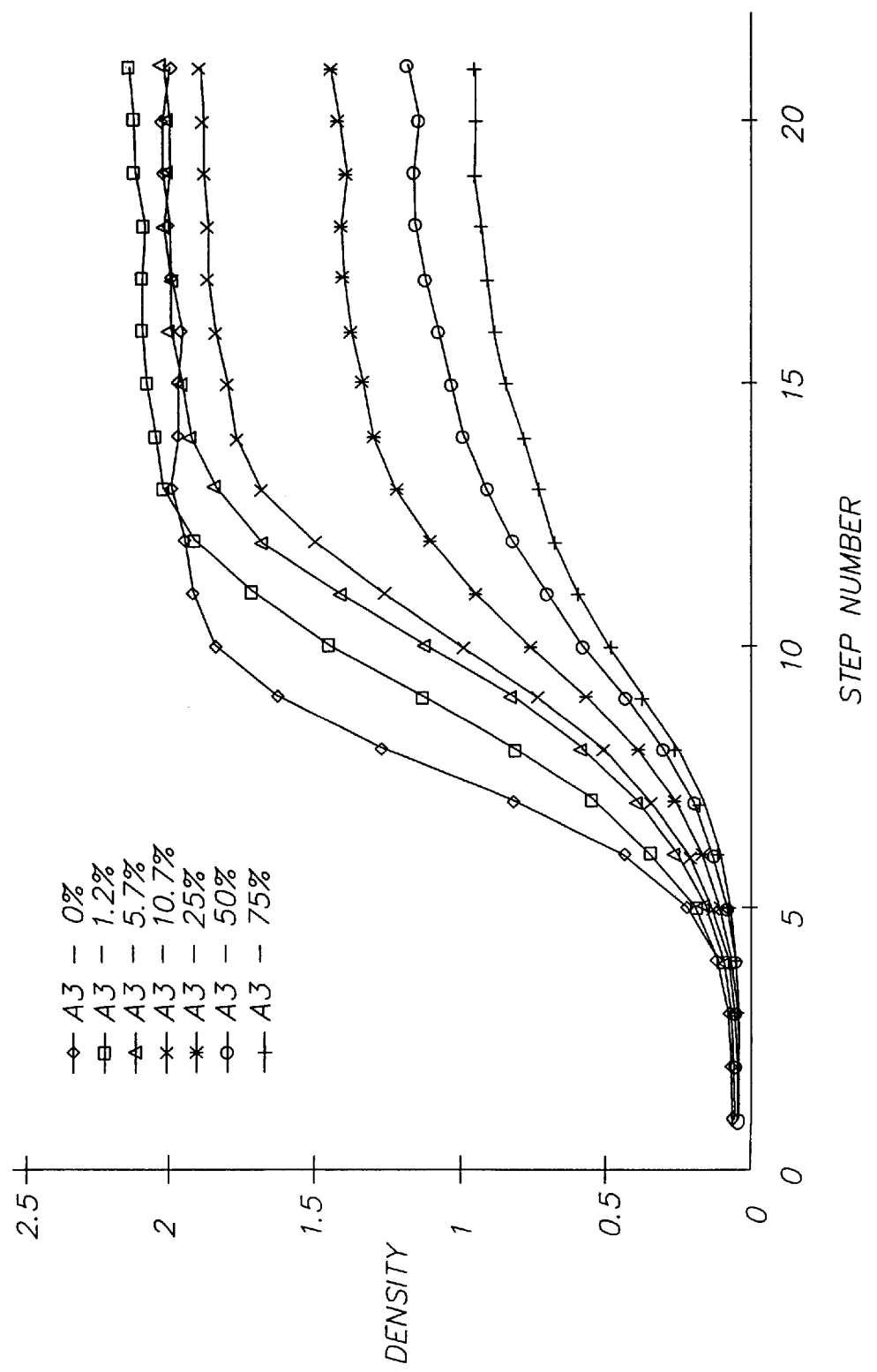
FIG. 1 shows plots of density vs. log exposure or step number (DlogE curves) for a series of low percentage incorporations (controls) and a series of high percentage incorporations (the invention) of a yellow DIR with a yellow image coupler.

As used herein and throughout the specification the term 'silver chloride' refers to a silver halide emulsion in which at least 50%, preferably at least 70%, more preferably at least 90% of the silver halide is silver chloride. In a particular embodiment the emulsion has T-grain morphology as discussed hereinafter.

As noted above, the photographic element contains a DI(A)R coupler of formula I or II. In formulae I and II, Z is a moiety which can react with oxidized developer to release the coupling-off group. In preferred embodiments of the invention, Z is selected from β-dicarbonyl compounds, such as acylacetanilides, β-ketoketones and β-ketoesters, and indanones, pyrazolones, pyrazoloazoles, phenols, and naphthols. The number of carbon atoms in $R_1$ and all $R_2$ substituents is preferably from 2 to 15.

Preferably j is 0 but when j is 1 or 2 the timing group(s) present in the DI(A)R coupler speed or slow release of a photographically useful group (PUG).

In a preferred embodiment of the invention, the DI(A)R coupler of formula I or II is of formula III or IV, respectively:

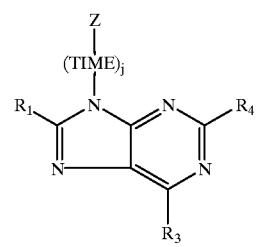

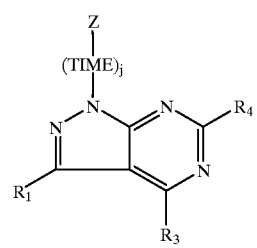

wherein:
- Z is as described above;
- $R_1$ is as described above; and
- each of $R_3$ and $R_4$ is a hydrogen atom or as described above for $R_2$ with the proviso that at least one of $R_1$, $R_3$ and $R_4$ is not a hydrogen atom.

Preferably the total number of carbon atoms in groups $R_1$, $R_3$ and $R_4$ taken together is at least 2, more preferably from 2 to 15 carbon atoms.

The use of Hammett sigma values to describe chemical properties is well established in the literature and is discussed, for example, in "Exploring QSAR, fundamentals and Applications in Chemistry and Biology", C. Hansch and A. Leo, American Chemical Society, Washington, D.C. 1995; "The Chemists Companion", A. J. Gorden and R. A. Ford, John Wiley & Sons, New York, 1979; and A. Leo in "Comprehensive Medicinal Chemistry", edited by C. Hansch, P. G. Sammes, and J. B. Taylor, Permagon Press, New York, 1972. Generally, sigma values increase with increasing electron-withdrawing power of the substituent. The sigma value for hydrogen is equal to zero.

In another preferred embodiment of the invention, the DIR coupler of formula III or IV is of formula V or VI, respectively:

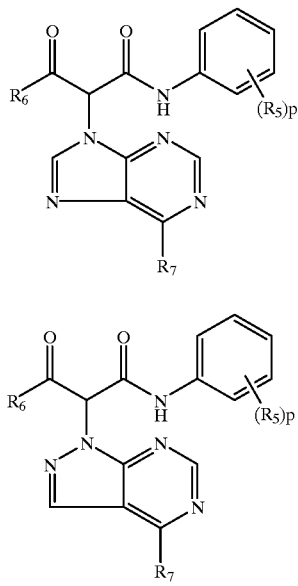

wherein:
each of the $R_5$ substituents is a halogen atom, a cyano group or a group selected from an unsubstituted or substituted alkyl, aryl, alkoxy, aryloxy, acyloxy, alkyl- or aryl-thio, carbonamido, carbamoyl, alkoxy- or aryloxy-carbonyl, alkyl- or aryl-carbonyl, sulfonyl, sulfonamido, sulfoxyl, and sulfonate group;

$R_6$ is selected from the group consisting of an unsubstituted or substituted tertiary alkyl, aryl, heterocyclic and alkyl-and aryl-amino groups;

$R_7$ is as defined above for $R_2$ and p is from 0 to 5.

Preferably one of the $R_5$ substituents is a halogen atom or an unsubstituted or substituted alkoxy group in the 2-position relative to the anilino nitrogen atom and there may be optionally one further $R_5$ substituent in the 4- or 5-position which comprises a halogen atom, cyano group or an unsubstituted or substituted alkyl, phenyl, carbonamido, carbamoyl, alkoxy- or aryloxy-carbonyl, sulfonamido, sulfamoyl, acyloxy, acyl, alkyl- or aryl-sulfonyl, sulfoxyl, sulfonate or trifluoro-methyl group.

When $R_6$ is a heterocycle it may be, for example, a pyrrole, indole, pyridine, thiophene, furan, quinoline, benzofuran, benzothiophene, pyrimidine, pyridazine, imidazole, benzimidazole, indazole or pyrazole. $R_6$ is preferably selected from the group consisting of an unsubstituted or substituted tertiary alkyl group or a phenyl group. $R_7$ is preferably an unsubstituted or substituted alkyl- or aryl-thio group, alkoxy or aryloxy group, alkyl-or aryl-amino group, a carbonamido group represented by —$NHCOR_{10}$ where $R_{10}$ is an alkyl or an unsubstituted or substituted phenyl, alkoxy or phenoxy. More preferably $R_7$ contains at least two carbon atoms and in one useful embodiment $R_7$ is a hydrolyzable —$SCH_2CO_2R_{11}$ group where $R_{11}$ is an alkyl or aryl group. In a further preferred embodiment $R_7$ is an alkoxy or alkylamino group.

In a further preferred embodiment of the invention, the DIR coupler of formula III or IV is of formula VII or VIII, respectively:

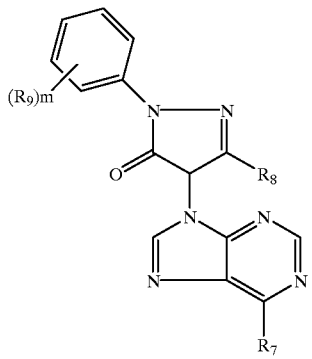

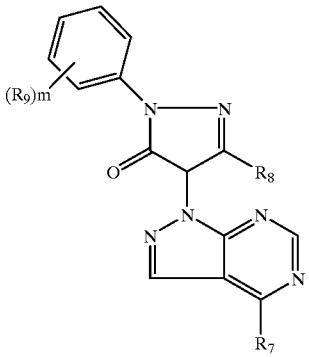

wherein
$R_7$ is as hereinbefore defined,
$R_8$ is an unsubstituted or substituted alkyl, aryl, alkyl- or aryl-amino or carbonamido group,
$R_9$ is as defined above for $R_5$ and
m is from 0 to 5.

Preferred groups for $R_7$ are those listed as preferred for compounds of formulae V and VI.

As used herein and throughout the specification the term alkyl refers to an unsaturated or saturated straight or branched chain alkyl group having 1–25 atoms and includes cycloalkyl having 3–8 carbon atoms. The term aryl includes aralkyl (and specifically fused aryl within its scope). The term heterocyclic specifically includes fused heterocyclic within its scope.

Any substituent may be chosen to further substitute the $R_1$-$R_{11}$ groups of this invention that does not adversely affect the performance of the DI(A)R couplers of this invention. When the term "group" is applied to the identification of a substituent containing a substitutable hydrogen, it is intended to encompass not only the substituent's unsubstituted form, but also its form further substituted with any group or groups as herein mentioned. As used herein any tautomeric forms are considered to be within the scope of the invention.

Suitably, the group may be halogen or may be bonded to the remainder of the molecule by an atom of carbon, silicon, oxygen, nitrogen, phosphorus, or sulfur. The substituent may be, for example, halogen, such as chlorine, bromine or fluorine; nitro; hydroxyl; cyano; carboxyl; or groups which may be further substituted, such as alkyl, including straight or branched chain alkyl, such as methyl, trifluoromethyl, ethyl, t-butyl, 3-(2,4-di-t-pentylphenoxy) propyl, and tetradecyl; alkenyl, such as ethylene, 2-butene; alkoxy, such as methoxy, ethoxy, propoxy, butoxy, 2-methoxy-ethoxy, sec-butoxy, hexyloxy, 2-ethylhexyloxy, tetra-decyloxy, 2-(2,4-di-t-pentylphenoxy)ethoxy, and 2-do-decyloxy-ethoxy; aryl such as phenyl, 4-t-butylphenyl, 2,4,6-trimethylphenyl, naphthyl; aryloxy, such as phenoxy, 2-methylphenoxy, alpha- or beta-naphthyloxy, and 4-tolyl-oxy; carbonamido, such as acetamido, benzamido, butyramido, tetradecanamido, alpha-(2,4-di-t-pentyl-phenoxy) acetamido, alpha-(2,4-di-t-pentylphenoxy)butyramido, alpha-(3-pentadecylphenoxy)hexanamido, alpha-(4-hydroxy-3-t-butylphenoxytetradecanamido, 2-oxo-pyrrolidin-1-yl, 2-oxo-5-tetradecylpyrrolidin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylamino, ethoxyarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl)carbonylamino, p-dodecylphenylcarbonylamino, p-toluylcarbonylamino, N-methylureido, N,N-dimethylureido, N-methyl-N-dodecylureido, N-hexadecylureido, N,N-dioctadecyl-ureido, N,N-di-octyl-N'-ethylureido, N-phenylureido, N,N-diphenyl-ureido, N-phenyl-N-p-toluylureido, N-(m-hexadecylphenyl)ureido, N,N-(2,5-di-t-pentylphenyl)-N'-ethylureido, and t-butylcarbonamido; sulfonamido, such as methylsulfonamido, benzenesulfonamido, p-toluylsulfonamido, p-dodecylbenzenesulfonamido, N-methyltetradecylsulfonamido, N,N-di-propylsulfamoylamino, and hexadecylsulfonamido; sulfamoyl, such as N-methylsulfamoyl, N-ethylsulfamoyl, N,N-dipropyl-sulfamoyl, N-hexadecylsulfamoyl, N,N-dimethyl-sulfamoyl; N-[3-(dodecyloxy)-propyl]sulfamoyl, N-[4-(2,4-di-t-pentylphenoxybutyl]-sulfamoyl, N-methyl-N-tetradecylsulfamoyl, and N-dodecylsulfamoyl; carbamoyl, such as N-methylcarbamoyl, N,N-dibutyl-carbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl; acyl, such as acetyl, (2,4-di-t-amylphenoxy)acetyl, phenoxycarbonyl, p-dodecyloxyphenoxycarbonyl, methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxy-sulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-toluylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecyl-sulfinyl, phenylsulfinyl, 4-nonylphenylsulfinyl, and p-toluylsulfinyl; thio, such as ethylthio, octylthio, benzylthio, tetradecylthio, 2-(2,4-di-t-pentyl-phenoxy) ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; imido, such as 1 (N-phenylimido)ethyl, N-succinimido or 3-benzylhydantoinyl; phosphate, such as dimethylphosphate and ethylbutylphosphate; phosphite, such as diethyl and dihexylphosphite; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen and sulfur, such as 2-furyl, 2-thienyl, 2-benzimidazolyloxy or 2-benzo-thiazolyl; quaternary ammonium, such as triethylammonium; and silyloxy, such as trimethylsilyloxy.

If desired, the substituents may themselves be further substituted one or more times with the described substituent groups. The particular substituents used may be selected by those skilled in the art to attain the desired photographic properties for a specific application and can include, for example, hydrophobic groups, solubilizing groups, blocking groups, releasing or releasable groups and groups which adsorb to silver halide. Generally, the above groups and substituents thereof may include those having up to 48 carbon atoms, typically 1 to 36 carbon atoms and usually less than 24 carbon atoms, but greater numbers are possible depending on the particular substituents selected.

A timing group TIME as in formulae I, II, III and IV produces the time-delayed release of a photographically useful group (PUG), such groups using an intramolecular nucleophilic substitution reaction (U.S. Pat. No. 4,248,962); groups utilizing an electron transfer reaction along a conjugated system (U.S. Pat. No. 4,409,323; 4,421,845; 4,861,701, Japanese Applications 57-188035; 58-98728; 58-209736; 58-209738); groups that function as a coupler or reducing agent after the coupler reaction (U.S. Pat. No. 4,438,193; U.S. Pat. No. 4,618,571) and groups that combine the features described above.

Examples of the DI(A)R couplers used in elements of this invention include but are not limited to structures A1 to A37 below:

A1

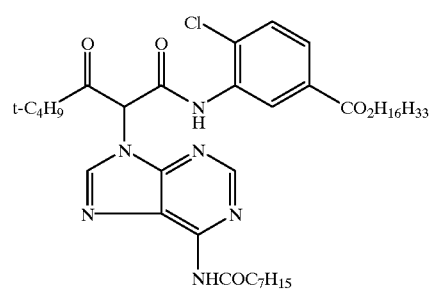

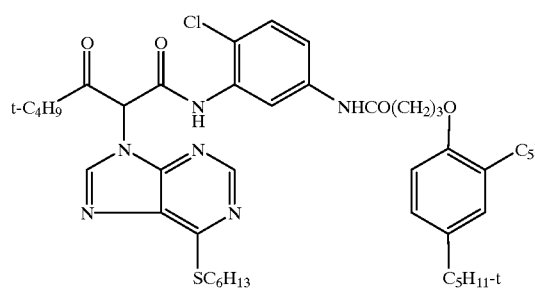
A2
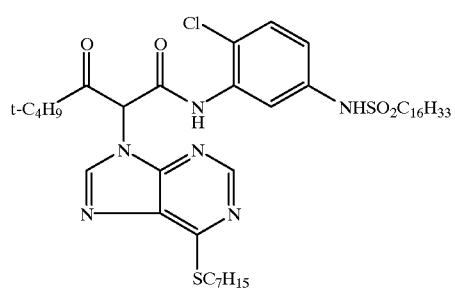
A3
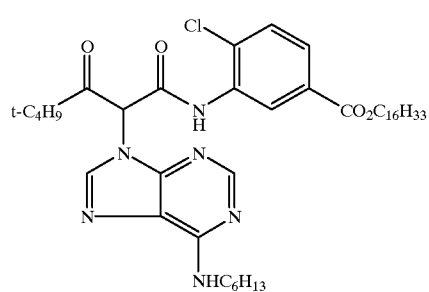
A4
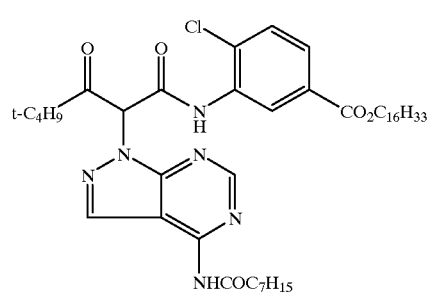
A5
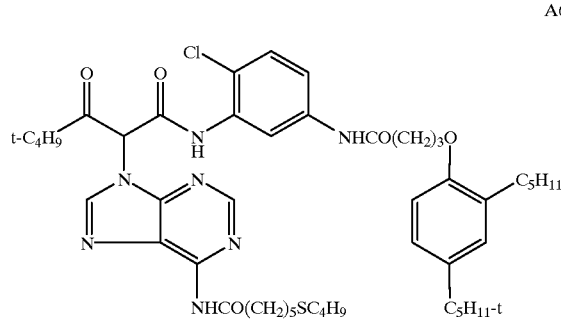
A6
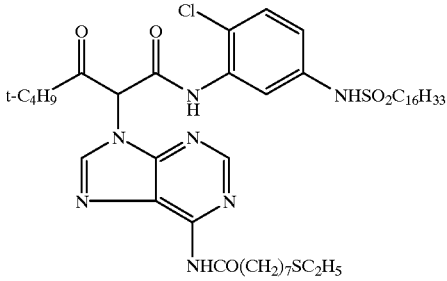
A7
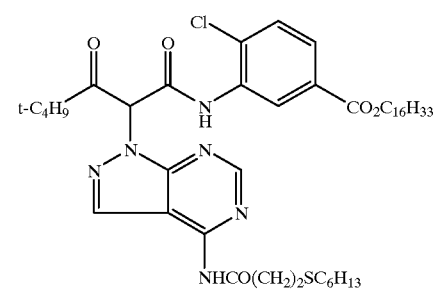
A8
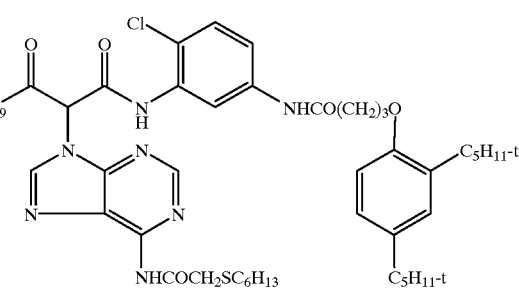
A9
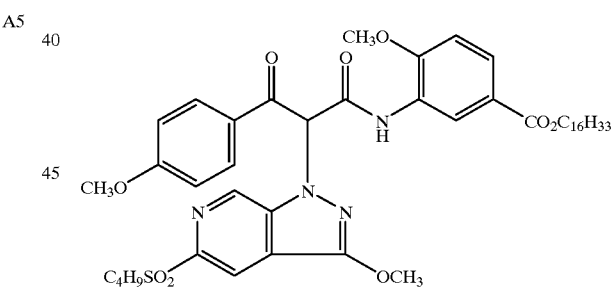
A10
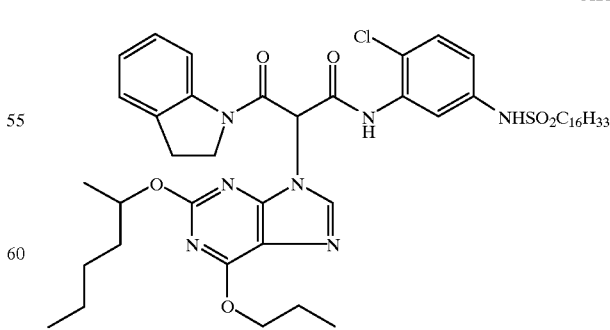
A11

-continued
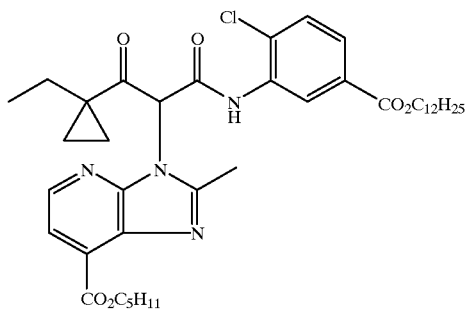
A12
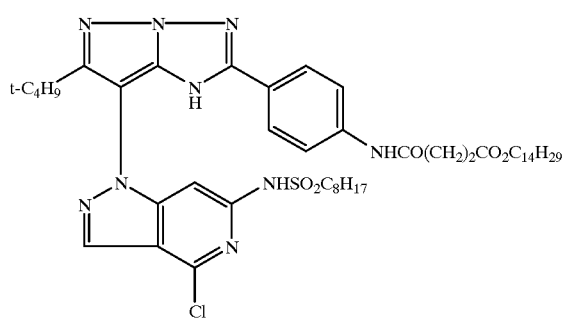
A13
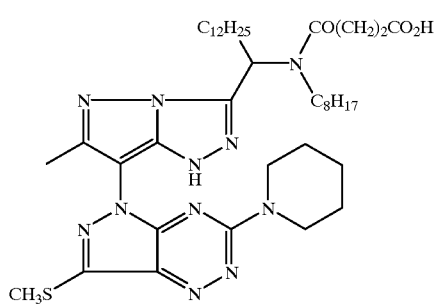
A14
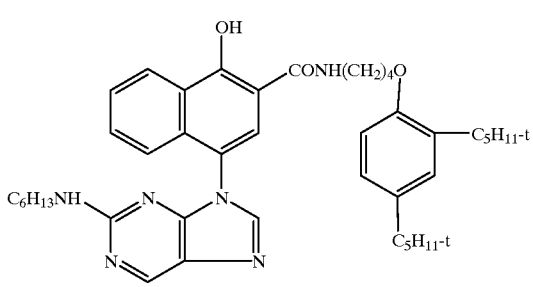
A15
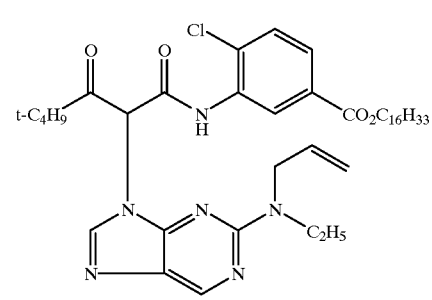
A16
-continued
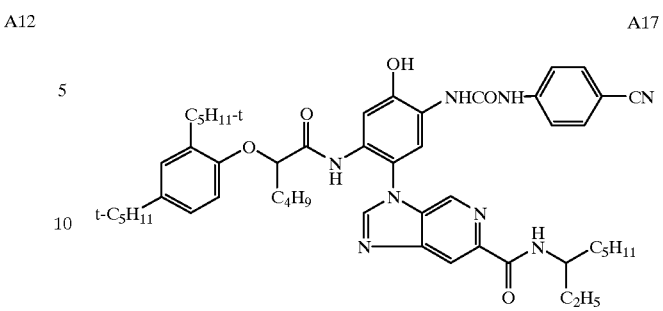
A17
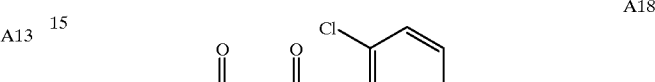
A18
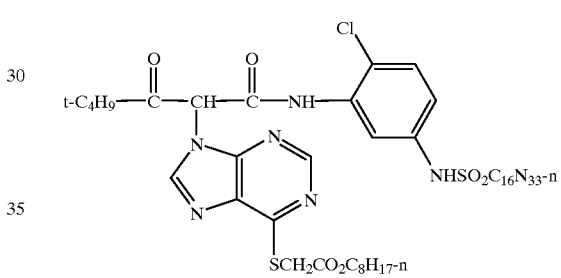
A19
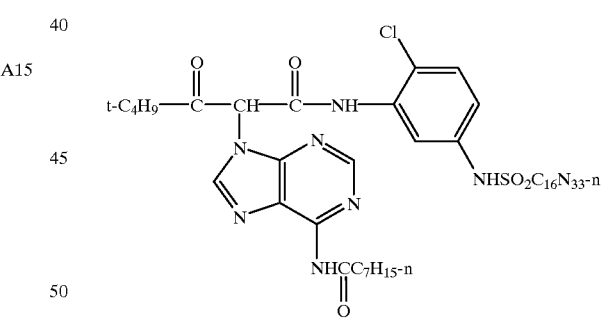
A20
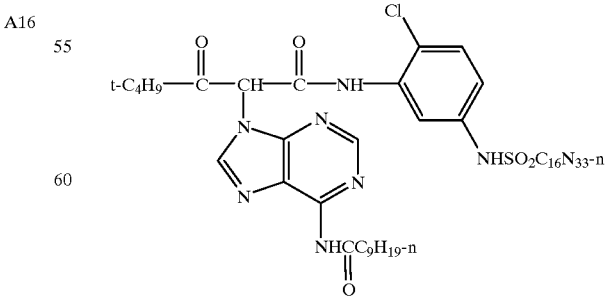
A21

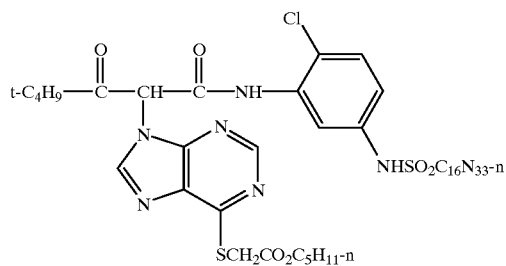
A22
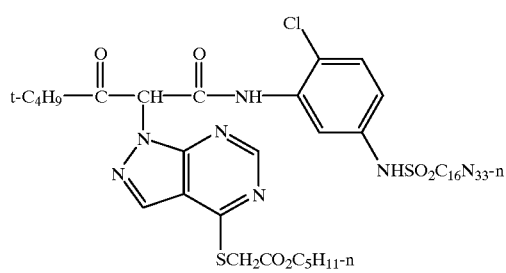
A23
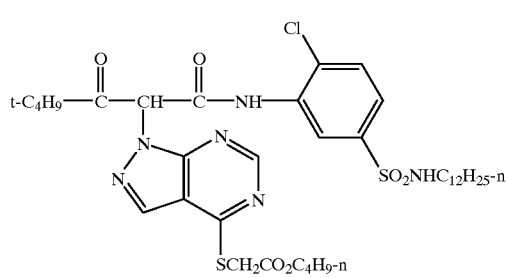
A24
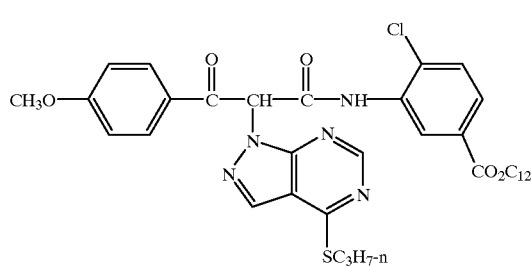
A25
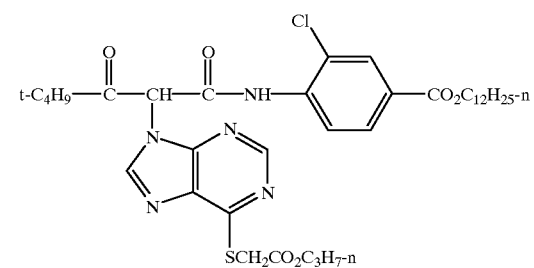
A26
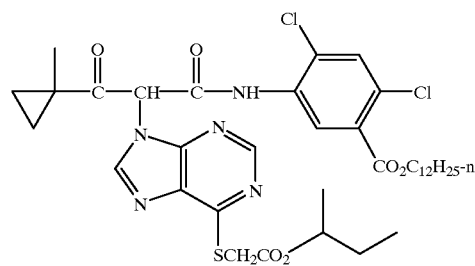
A27
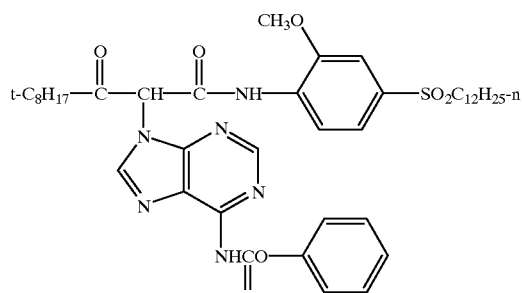
A28
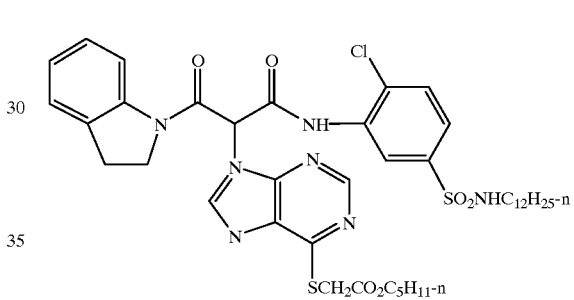
A29
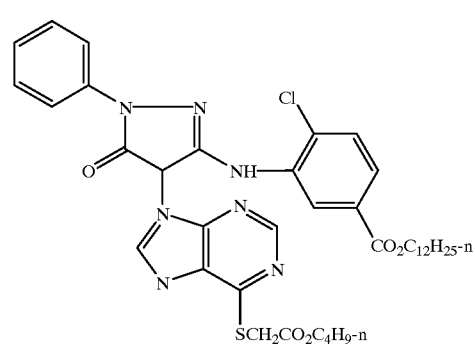
A30
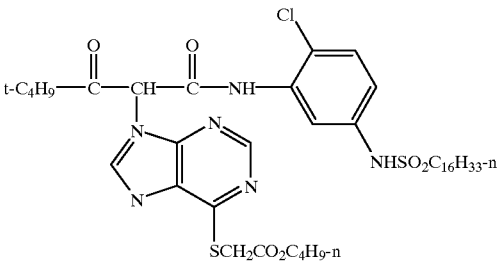
A31

-continued
A32
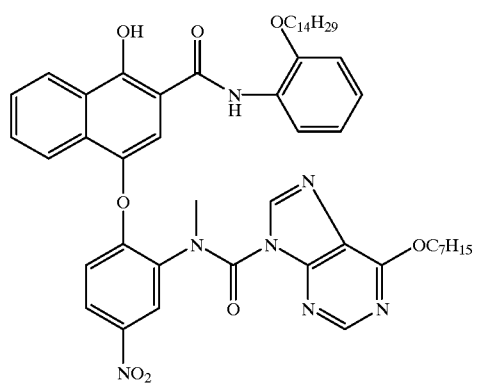
A33
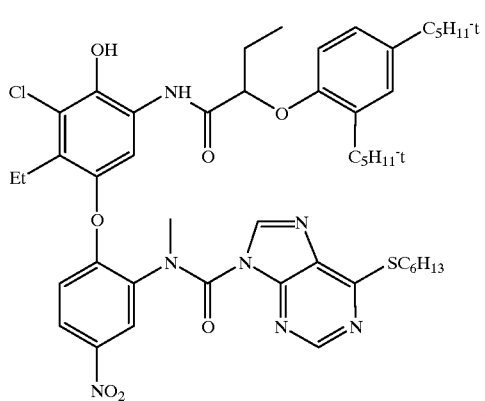
A34
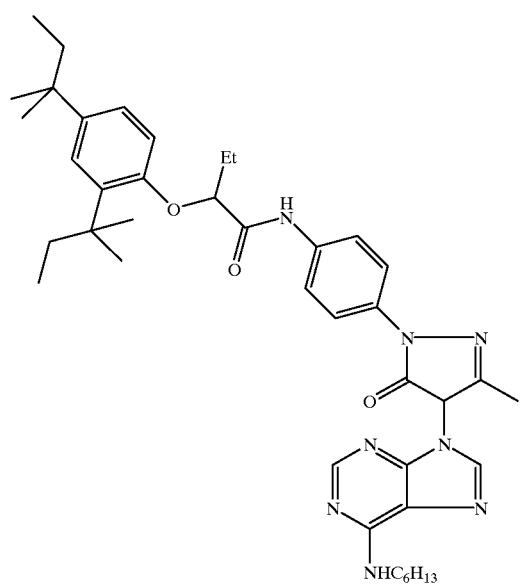
-continued
A35
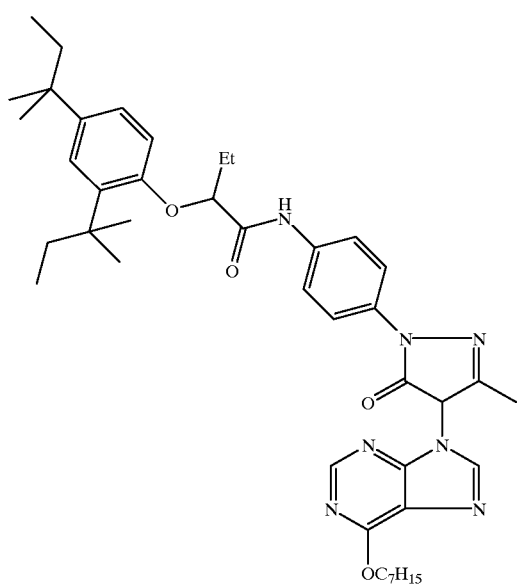
A36
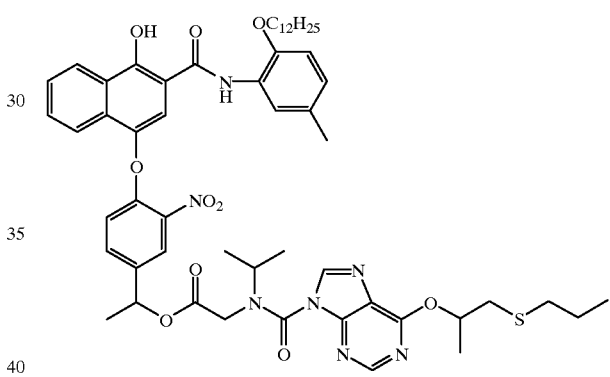
A37
According to the present invention the DI(A)R coupler comprises from 25 to about 90% of the total amount of coupler, wherein the total amount of coupler is defined as the sum of the moles of the image coupler and the number of moles of the DI(A)R coupler. Preferably the DI(A)R coupler comprises about 30 to about 80% and more preferably about 50 to about 75% of the total amount of coupler.

The image and DI(A)R couplers employed in the invention are usually utilized by dissolving them in high-boiling coupler solvents and then dispersing the organic coupler plus coupler solvent mixtures as small particles in aqueous solutions of gelatin and surfactant (via milling or homogenization). Removable auxiliary organic solvents such as ethyl acetate or cyclohexanone may also be used in the preparation of such dispersions to facilitate the dissolution of the coupler in the organic phase. Coupler solvents useful for the practice of this invention include aryl phosphates (e.g. tritolyl phosphate), alkyl phosphates (e.g. trioctyl phosphate), mixed aryl alkyl phosphates (e.g. diphenyl 2-ethylhexyl phosphate), aryl, alkyl or mixed aryl alkyl phosphonates, phosphine oxides (e.g. trioctylphosphine oxide), esters of aromatic acids (e.g. dibutyl phthalate, octyl benzoate, or benzyl salicylate) esters of aliphatic acids (e.g. acetyl tributyl citrate or dibutyl sebecate), alcohols (e.g. 2-hexyl-1-decanol), phenols (e.g. p-dodecylphenol), carbonamides (e.g. N,N-dibutyldodecanamide or N-butylacetanalide), sulfoxides (e.g. bis(2-ethylhexyl) sulfoxide), sulfonamides (e.g. N,N-dibutyl-p-toluenesulfonamide) or hydrocarbons (e.g. dodecylbenzene). Additional coupler solvents and auxiliary solvents are noted in Research Disclosure, December 1989, Item 308119, p 993. Useful coupler:coupler solvent weight ratios range from about 1:0.1 to 1:8.0, with 1:0.2 to 1:4.0 being preferred.

The image couplers and DI(A)R couplers of this invention are employed in colour photographic elements. Such elements typically contain at least one silver halide emulsion sensitive to blue light, at least one silver halide emulsion sensitive to green light and at least one silver halide emulsion sensitive to red light, at least one of the silver halide emulsions comprising at least 50% silver chloride. The DI(A)R couplers used in this invention are particularly advantageous when included in a silver chloride emulsion sensitive to blue light.

The emulsion layer of the photographic element of the invention can comprise any one or more of the light sensitive layers of the photographic element. The photographic elements made in accordance with the present invention can be single colour elements or multicolour elements. Multicolour elements contain dye image-forming units sensitive to each of the three primary regions of the spectrum. Each unit can be comprised of a single emulsion layer or of multiple emulsion layers sensitive to a given region of the spectrum. The layers of the element, including the layers of the image-forming units, can be arranged in various orders as known in the art. In an alternative format, the emulsions sensitive to each of the three primary regions of the spectrum can be disposed as a single segmented layer.

A typical multicolour photographic element comprises a support bearing a cyan dye image-forming unit comprised of at least one red-sensitive silver halide emulsion layer having associated therewith at least one cyan dye-forming coupler, a magenta dye image-forming unit comprising at least one green-sensitive silver halide emulsion layer having associated therewith at least one magenta dye-forming coupler, and a yellow dye image-forming unit comprising at least one blue-sensitive silver halide emulsion layer having associated therewith at least one yellow dye-forming coupler, wherein at least one of the silver halide emulsions comprises at least 50% of silver chloride emulsion. The element can contain additional layers, such as filter layers, interlayers, overcoat layers, subbing layers, and the like. All of these can be coated on a support which can be transparent or reflective (for example, a paper support).

Photographic elements of the present invention may also usefully include a magnetic recording material as described in Research Disclosure, Item 34390, November 1992, or a transparent magnetic recording layer such as a layer containing magnetic particles on the underside of a transparent support as in U.S. Pat. No. 4,279,945 and U.S. Pat. No. 4,302,523. The element typically will have a total thickness (excluding the support) of from 5 to 30 $\mu$m. While the order of the colour sensitive layers can be varied, they will normally be red-sensitive, green-sensitive and blue-sensitive, in that order on a transparent support, (that is, blue sensitive furthest from the support) and the reverse order on a reflective support being typical.

The present invention also contemplates the use of photographic elements of the present invention in what are often referred to as single use cameras (or "film with lens" units). These cameras are sold with film preloaded in them and the entire camera is returned to a processor with the exposed film remaining inside the camera. Such cameras may have glass or plastic lenses through which the photographic element is exposed.

In the following discussion of suitable materials for use in elements of this invention, reference will be made to Research Disclosure, September 1996, Number 389, Item 38957, which will be identified hereafter by the term "Research Disclosure I." The Sections hereafter referred to are Sections of the Research Disclosure I unless otherwise indicated. All Research Disclosures referenced are published by Kenneth Mason Publications, Ltd., Dudley Annex, 12a North Street, Emsworth, Hampshire P010 7DQ, ENGLAND.

The silver chloride emulsions employed in the photographic elements of the present invention may be negative-working, such as surface-sensitive emulsions or unfogged internal latent image forming emulsions, or positive working emulsions of the internal latent image forming type (that are fogged during processing). Suitable emulsions and their preparation as well as methods of chemical and spectral sensitization are described in Sections I through V. Colour materials and development modifiers are described in Sections V through XX. Vehicles which can be used in the photographic elements are described in Section II, and various additives such as brighteners, antifoggants, stabilizers, light absorbing and scattering materials, hardeners, coating aids, plasticizers, lubricants and matting agents are described, for example, in Sections VI through XIII. Manufacturing methods are described in all of the sections, layer arrangements particularly in Section XI, exposure alternatives in Section XVI, and processing methods and agents in Sections XIX and XX.

With negative working silver halide a negative image can be formed. Optionally a positive (or reversal) image can be formed although a negative image is typically first formed.

The photographic elements of the present invention may also use coloured couplers (e.g. to adjust levels of interlayer correction) and masking couplers such as those described in EP 213 490; Japanese Published Application 58-172,647; U.S. Pat. No. 2,983,608; German Application DE 2,706, 117C; U.K. Patent 1,530,272; Japanese Application A-113935; U.S. Pat. No. 4,070,191 and German Application DE 2,643,965. The masking couplers may be shifted or blocked.

The photographic elements may also contain materials that accelerate or otherwise modify the processing steps of bleaching or fixing to improve the quality of the image. Bleach accelerators described in EP 193 389; EP 301 477; U.S. Pat. No. 4,163,669; U.S. Pat. No. 4,865,956; and U.S. Pat. No. 4,923,784 are particularly useful. Also contemplated is the use of nucleating agents, development accelerators or their precursors (UK Patent 2,097,140; U.K. Patent 2,131,188); development inhibitors and their precursors (U.S. Pat. No. 5,460,932; U.S. Pat. No. 5,478,711); electron transfer agents (U.S. Pat. No. 4,859,578; U.S. Pat. No. 4,912,025); antifogging and anti color-mixing agents such as derivatives of hydroquinones, aminophenols, amines, gallic acid; catechol; ascorbic acid; hydrazides; sulfonamidophenols; and non colour-forming couplers.

The elements may also contain filter dye layers comprising colloidal silver sol or yellow and/or magenta filter dyes and/or antihalation dyes (particularly in an undercoat beneath all light sensitive layers or in the side of the support opposite that on which all light sensitive layers are located) either as oil-in-water dispersions, latex dispersions or as solid particle dispersions. Additionally, they may be used with "smearing" couplers (e.g. as described in U.S. Pat. No. 4,366,237; EP 096 570; U.S. Pat. No. 4,420,556; and U.S. Pat. No. 4,543,323.) Also, the couplers may be blocked or coated in protected form as described, for example, in Japanese Application 61/258,249 or U.S. Pat. No. 5,019,492.

The photographic elements may further contain other image-modifying compounds such as other DI(A)R's. Additional DI(A)R's for elements of the present invention, are known in the art and examples are described in U.S. Pat. Nos. 3,137,578; 3,148,022; 3,148,062; 3,227,554; 3,384,657; 3,379,529; 3,615,506; 3,617,291; 3,620,746; 3,701,783; 3,733,201; 4,049,455; 4,095,984; 4,126,459; 4,149,886; 4,150,228; 4,211,562; 4,248,962; 4,259,437; 4,362,878; 4,409,323; 4,477,563; 4,782,012; 4,962,018; 4,500,634; 4,579,816; 4,607,004; 4,618,571; 4,678,739; 4,746,600; 4,746,601; 4,791,049; 4,857,447; 4,865,959; 4,880,342; 4,886,736; 4,937,179; 4,946,767; 4,948,716; 4,952,485; 4,956,269; 4,959,299; 4,966,835; 4,985,336 as well as in patent publications GB 1,560,240; GB 2,007,662; GB 2,032,914; GB 2,099,167; DE 2,842,063, DE 2,937,127; DE 3,636,824; DE 3,644,416 as well as the following European Patent Publications: 272,573; 335,319; 336,411; 346,899; 362,870; 365,252; 365,346; 373,382; 376,212; 377,463; 378,236; 384,670; 396,486; 401,612; 401,613.

DI(A)R compounds are also disclosed in "Developer-Inhibitor-Releasing (DI(A)R) Couplers for Color Photography," C. R. Barr, J. R. Thirtle and P. W. Vittum in *Photographic Science and Engineering*, Vol. 13, p. 174 (1969).

It is also contemplated that the concepts of the present invention may be employed to obtain reflection color prints as described in *Research Disclosure*, November 1979, Item 18716, available from Kenneth Mason Publications, Ltd, Dudley Annex, 12a North Street, Emsworth, Hampshire P0101 7DQ, England. The emulsions and materials to form elements of the present invention, may be coated on pH adjusted support as described in U.S. Pat. No. 4,917,994; with epoxy solvents (EP 0 164 961); with additional stabilizers (as described, for example, in U.S. Pat. No. 4,346,165; U.S. Pat. No. 4,540,653 and U.S. Pat. No. 4,906,559); with ballasted chelating agents such as those in U.S. Pat. No. 4,994,359 to reduce sensitivity to polyvalent cations such as calcium; and with stain reducing compounds such as described in U.S. Pat. No. 5,068,171 and U.S. Pat. No. 5,096,805. Other compounds which may be useful in the elements of the invention are disclosed in Japanese Published Applications 83-09,959; 83-62,586; 90-072,629; 90-072,630; 90-072,632; 90-072,633; 90-072,634; 90-077,822; 90-078,229; 90-078,230; 90-079,336; 90-079,338; 90-079,690; 90-079,691; 90-080,487; 90-080,489; 90-080,490; 90-080,491; 90-080,492; 90-080,494; 90-085,928; 90-086,669; 90-086,670; 90-087,361; 90-087,362; 90-087,363; 90-087,364; 90-088,096; 90-088,097; 90-093,662; 90-093,663; 90-093,664; 90-093,665; 90-093,666; 90-093,668; 90-094,055; 90-094,056; 90-101,937; 90-103,409; 90-151,577.

Although at least 50% of the silver halide is silver chloride, as hereinbefore defined, the balance generally consists of bromide, iodide or a mixture thereof. The silver chloride grains used in the invention may have a variety of morphologies, such as cubic, but tabular grain silver chloride emulsions are preferred. The grain size of the silver chloride may have any distribution known to be useful in photographic compositions, and may be either polydispersed or monodispersed.

Tabular grains are those with two parallel major faces each clearly larger than any remaining grain face and tabular grain emulsions are those in which the tabular grains account for at least 30%, more typically at least 50%, preferably >70% and optimally >90% of total grain projected area. The tabular grains can account for substantially all (>97%) of total grain projected area. The tabular grain emulsions can be high aspect ratio tabular grain emulsions—i.e., ECD/t>8, where ECD is the diameter of a circle having an area equal to grain projected area and t is tabular grain thickness; intermediate aspect ratio tabular grain emulsions—i.e., ECD/t=5 to 8; or low aspect ratio tabular grain emulsions—i.e., ECD/t=2 to 5. The emulsions typically exhibit high tabularity (T), where T (i.e., $ECD/t^2$)>25 and ECD and t are both measured in micrometers ($\mu$m). The tabular grains can be of any thickness compatible with achieving an aim average aspect ratio and/or average tabularity of the tabular grain emulsion. Preferably the tabular grains satisfying projected area requirements are those having thicknesses of <0.3 $\mu$m, thin (<0.2 $\mu$m) tabular grains being specifically preferred and ultrathin (<0.07 $\mu$m) tabular grains being contemplated for maximum tabular grain performance enhancements.

Tabular grains formed of silver chloride that form a face-centered cubic (rock salt type) crystal lattice structure can have either {100} or {111} major faces. Emulsions containing {111} major face tabular grains, including those with controlled grain dispersities, chloride distributions, twin plane spacing, edge structures and grain dislocations as well as adsorbed {111} grain face stabilizers, are illustrated in those references cited in *Research Disclosure I*, Section I.B. (3) (page 503).

The silver halide grains to be used in the invention may be prepared according to methods known in the art, such as those described in *Research Disclosure I* and James, *The Theory of the Photographic Process*. These include methods such as ammoniacal emulsion making, neutral or acidic emulsion making, and others known in the art. These methods generally involve mixing a water soluble silver salt with a water soluble halide salt in the presence of a protective colloid, and controlling the temperature, pAg, pH values, etc., at suitable values during formation of the silver halide by precipitation.

In the course of grain precipitation one or more dopants (grain occlusions other than silver and halide) can be introduced to modify grain properties. For example, any of the various conventional dopants disclosed in *Research Disclosure*, Item 38957, Section I. Emulsion grains and their preparation, sub-section G. Grain modifying conditions and adjustments, paragraphs (3),(4) and (5), can be present in the emulsions of the invention. In addition it is specifically contemplated to dope the grains with transition metal hexa-coordination complexes containing one or more organic ligands, as taught by Olm et al U.S. Pat. No. 5,360,712.

It is specifically contemplated to incorporate in the face-centered cubic crystal lattice of the grains a dopant capable of increasing imaging speed by forming a shallow electron trap as discussed in Research Disclosure Item 36736 published November 1994.

The photographic elements of the present invention, as is typical, provide the silver chloride in the form of an emulsion. Photographic emulsions generally include a vehicle for coating the emulsion as a layer of a photographic element. Useful vehicles include both naturally occurring substances such as proteins, protein derivatives, cellulose derivatives (e.g., cellulose esters), gelatin (e.g., alkali-treated gelatin such as cattle bone or hide gelatin, or acid treated gelatin such as pigskin gelatin), deionized gelatin, gelatin derivatives (e.g., acetylated gelatin, phthalated gelatin, and the like), and others as described in *Research Disclosure I*. Also useful as vehicles or vehicle extenders are hydrophilic water-permeable colloids. These include synthetic polymeric peptizers, carriers, and/or binders such as poly(vinyl alcohol), poly(vinyl lactams), acrylamide polymers, polyvinyl acetals, polymers of alkyl and sulfoalkyl acrylates and methacrylates, hydrolyzed polyvinyl acetates, polyamides, polyvinyl pyridine, methacrylamide copolymers, and the like, as described in *Research Disclosure I*. The vehicle can be present in the emulsion in any amount useful in photographic emulsions. The emulsion can also include any of the addenda known to be useful in photographic emulsions.

The silver halide to be used in the invention may be advantageously subjected to chemical sensitization. Compounds and techniques useful for chemical sensitization of silver halide are known in the art and described in *Research Disclosure I* and the references cited therein. Compounds useful as chemical sensitizers, include, for example, active gelatin, sulfur, selenium, tellurium, gold, platinum, palladium, iridium, osmium, rhenium, phosphorous, or combinations thereof. Chemical sensitization is generally carried out at pAg levels of from 5 to 10, pH levels of from 4 to 8, and temperatures of from 30 to 80° C., as described in *Research Disclosure I*, Section IV (pages 510–511) and the references cited therein.

The silver halide may be sensitized by sensitizing dyes by any method known in the art, such as described in *Research Disclosure I*. The dye may be added to an emulsion of the silver halide grains and a hydrophilic colloid at any time prior to (e.g., during or after chemical sensitization) or simultaneous with the coating of the emulsion on a photographic element. The dyes may, for example, be added as a solution in water or an alcohol. The dye/silver halide emulsion may be mixed with a dispersion of colour image-forming coupler immediately before coating or in advance of coating (for example, 2 h).

Photographic elements of the present invention are preferably imagewise exposed using any of the known techniques, including those described in *Research Disclosure I*, section XVI. This typically involves exposure to light in the visible region of the spectrum, and typically such exposure is of a live image through a lens, although exposure can also be exposure to a stored image (such as a computer stored image) by means of light emitting devices (such as light emitting diodes, CRT and the like).

Photographic elements of the invention can be processed in any of a number of well-known photographic processes utilizing any of a number of well-known processing compositions, described, for example, in *Research Disclosure I*, or in T. H. James, editor, *The Theory of the Photographic Process*, 4th Edition, Macmillan, N.Y., 1977. In the case of processing a negative working element, the element is treated with a colour developer (that is one which will form the coloured image dyes with the colour couplers), and then with a oxidizer and a solvent to remove silver and silver halide. In the case of processing a reversal colour element, the element is first treated with a black and white developer (that is, a developer which does not form coloured dyes with the coupler compounds) followed by a treatment to fog silver halide (usually chemical fogging or light fogging), followed by treatment with a colour developer. Preferred colour developing agents are p-phenylenediamines. Especially preferred are:

4-amino N,N-diethylaniline hydrochloride,
4-amino-3-methyl-N,N-diethylaniline hydrochloride,
4-amino-3-methyl-N-ethyl-N-(β-(methanesulfonamido) ethylaniline sesquisulfate hydrate,
4-amino-3-methyl-N-ethyl-N-(β-hydroxyethyl)aniline sulfate,
4-amino-3-β-(methanesulfonamido)ethyl-N,N-diethylaniline hydrochloride and
4-amino-N-ethyl-N-(2-methoxyethyl)-m-toluidine di-p-toluene sulfonic acid.

Dye images can be formed or amplified by processes which employ in combination with a dye-image-generating reducing agent an inert transition metal-ion complex oxidizing agent, as illustrated by Bissonette U.S. Pat. Nos. 3,748,138, 3,826,652, 3,862,842 and 3,989,526 and Travis U.S. Pat. No. 3,765,891, and/or a peroxide oxidizing agent as illustrated by Matejec U.S. Pat. No. 3,674,490, *Research Disclosure*, Vol. 116, December, 1973, Item 11660, and Bissonette *Research Disclosure*, Vol. 148, August, 1976, Items 14836, 14846 and 14847. The photographic elements can be particularly adapted to form dye images by such processes as illustrated by Dunn et al U.S. Pat. No. 3,822,129, Bissonette U.S. Pat. Nos. 3,834,907 and 3,902,905, Bissonette et al U.S. Pat. No. 3,847,619, Mowrey U.S. Pat. No. 3,904,413, Hirai et al U.S. Pat. No. 4,880,725, Iwano U.S. Pat. No. 4,954,425, Marsden et al U.S. Pat. No. 4,983,504, Evans et al U.S. Pat. No. 5,246,822, Twist U.S. Pat. No. 5,324,624, Fyson EP-A-0 487 616, Tannahill et al WO 90/13059, Marsden et al WO 90/13061, Grimsey et al WO 91/16666, Fyson WO 91/17479, Marsden et al WO 92/01972. Tannahill WO 92/05471, Henson WO 92/07299, Twist WO 93/01524 and WO 93/11460 and Wingender et al German OLS 4,211, 460.

Development is followed by bleach-fixing, to remove silver or silver halide, washing and drying.

The following examples illustrate the synthesis and use of DIR couplers in accordance with the invention. Structures of Y-1 and M-1, which are yellow and magenta image dye-forming couplers respectively, and comparative DIR compounds CY-1, and CM-1 are given below:

Y-1
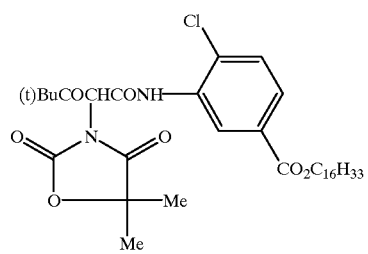
CY-1
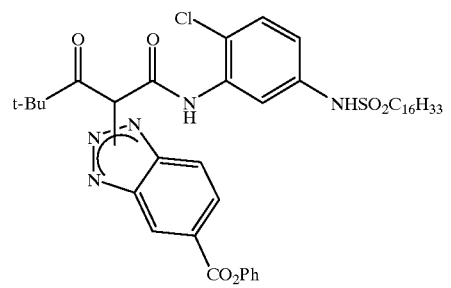
M-1
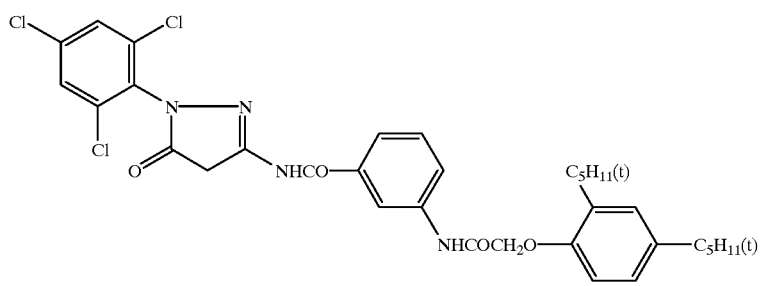
CM-1
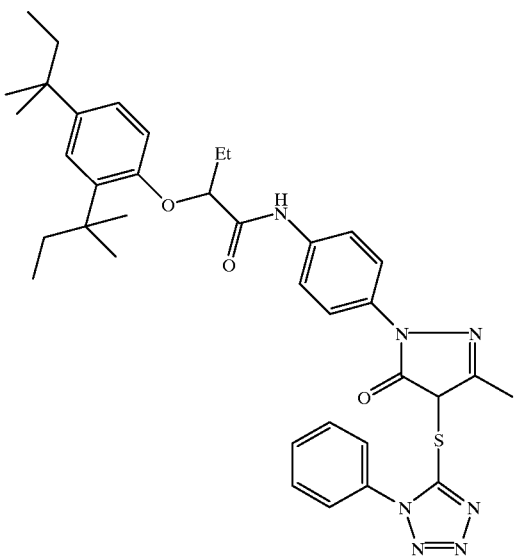
In the following syntheses, yields have not been optimised.
EXAMPLE 1
Synthesis of DIR Coupler A3
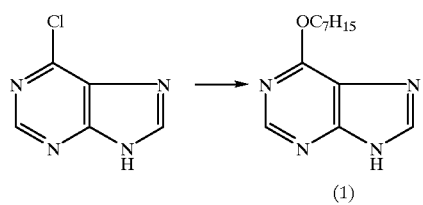
(1)
-continued
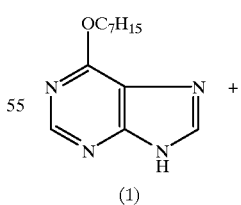
(1)
+
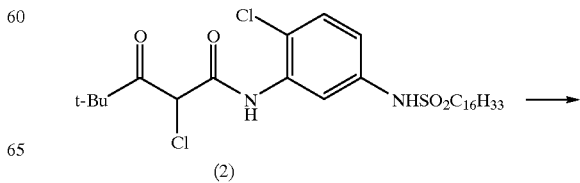
(2)
→

-continued

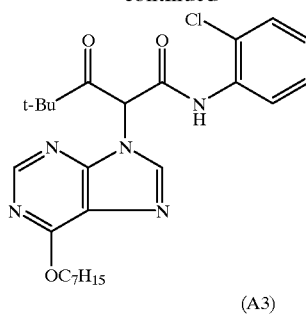

(A3)

(a) Preparation of 6-heptyloxypurine (1)

Heptanol (45.02 g, 0.388 mol) was added to a stirred suspension of a 60% dispersion of sodium hydride in oil (16.62 g, 0.416 mol) in dry tetrahydrofuran (350 ml) under an atmosphere of nitrogen. After gas evolution had ceased (about 1 h), 6-chloropurine (16.04 g, 0.104 mol) was added. The reaction began to foam and more gas was evolved. When gas evolution had ceased (about 0.75 h) the reaction was heated at reflux for 3 h then the solvent was removed in vacuo. The residual oily solid was suspended in water (2l) then concentrated hydrochloric acid (30 ml) was added. The aqueous suspension was neutralised with saturated sodium hydrogen carbonate solution and 60–80 petroleum ether (750 ml) added. The solid was moved from the biphasic mixture by filtration, washed with 60–80 petroleum ether and dried at oil-pump vacuum/40° C. This gave the title compound (1)(18.64 g, 79.7 mmol, 77%) as a white solid.

(b) Preparation of A3

Triethylamine (33 ml, 0.237 mol) was added to a stirred suspension of 6-heptyloxypurine (1) (18.64 g, 79.7 mmol) and (2) (CAS Reg.No. 67878-71-1)(47.03 g, 79.7 mmol) in dry dimethylformamide (200 ml) causing the solids to dissolve. The solution was heated at 60C for 3 h. The reaction was allowed to cool to room temperature then added with stirring to water (5l) containing concentrated hydrochloric acid (300 ml). The aqueous solution was decanted away from the sticky solid which formed. This solid was then dissolved in ether (500 ml). The organic solution was washed with water (3×300 ml), dried (magnesium sulfate) and concentrated in vacuo. The residual oil was passed through a silica plug (eluent 3:1 60–80 petroleum ether/ethyl acetate) to remove baseline material. The filtrate was concentrated in vacuo and recrystallised from 60–80 petroleum ether/ethyl acetate. The fine solid was removed by filtration through Kieselguhr and washed well with 60–80 petroleum ether. The filtrate was concentrated in vacuo to give an oil. The Kieselguhr was suspended in ethyl acetate (800 ml) and stirred for 1 h. The Kieselguhr was removed by filtration and the filtrate concentrated in vacuo giving the title compound (18.65 g, 23.7 mmol, 30%) as a fawn solid. The oil resulting from the filtration of the solid through Kieselguhr was purified by column chromatography over silica (eluent 3:1 60–80 petroleum ether/ethyl acetate) to give a further sample of the title compound (6.43 g, 8.15 mmol, 10%, total yield 40%).

EXAMPLE 2

Synthesis of DIR Coupler A35

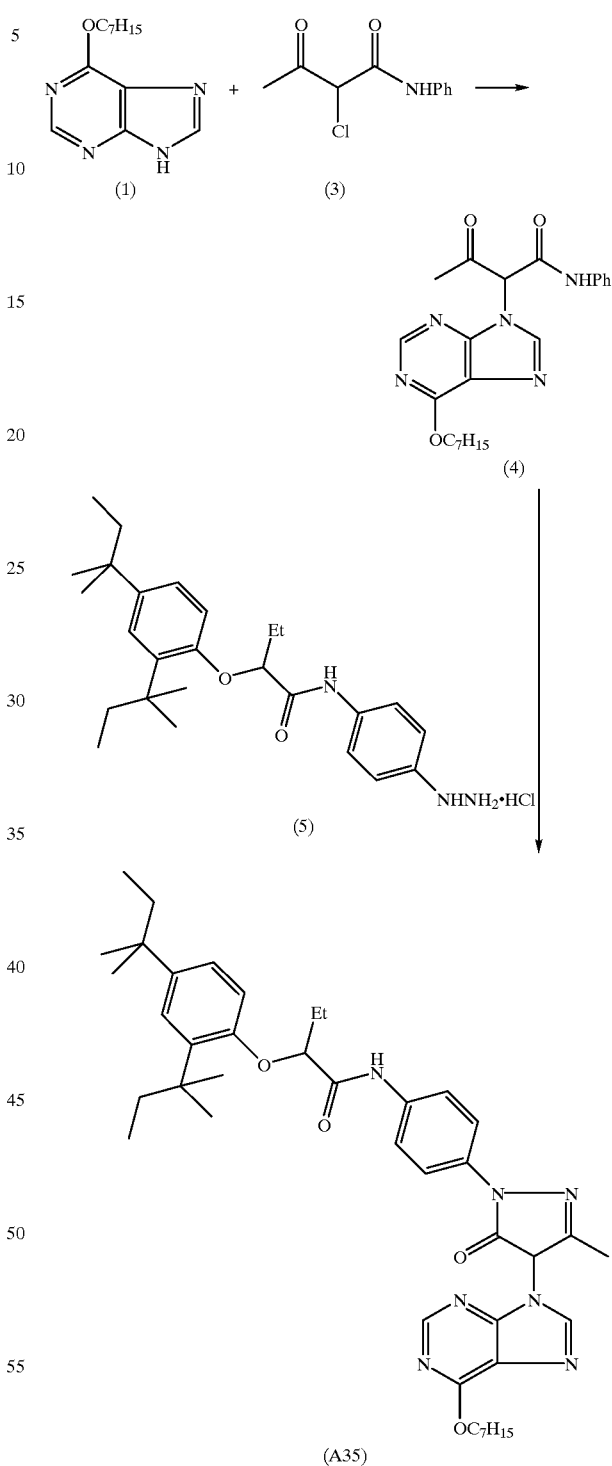

(c) Preparation of (4)

Tetramethylguanidine (34.56 g, 0.301 mol) was added to a stirred suspension of (3)(CAS Re. No. 31844-92-5) 18.35 g, 86.8 mmol) and (1) (23.42 g, 0.100 mol) in dimethylformamide (200 ml). Most of the solid dissolved at room temperature and the rest did as the reaction was heated to 75C. The reaction was stirred at this temperature for 1 h then was allowed to cool. The reaction was added to a mixture of water (2l) and concentrated hydrochloric acid (200 ml). After stirring for 1 h the liquid was decanted away from the sticky solid which had formed. This solid was recrystallised from ethanol to give the title compound (24.94 g, 61.0 mmol, 70%) as a white solid.

(d) Preparation of (A35)

A suspension of (4) (19.81 g, 48.4 mmol) and (5) (CAS Reg.No.209855-54-9)(22.28 g, 48.3 mmol) in acetic acid (150 ml) was heated at reflux for 1.5 h. Over that time the solid dissolved to give an orange solution. The majority of the acetic acid was removed in vacuo and the residue stirred in water (1.5l). The sticky solid was removed by filtration and recrystallised from ethyl acetate. The filtrate was concentrated in vacuo and the residual oil purified by column chromatography over silica (eluent 1:1 60–80 m petroleum ether/ethyl acetate the ethyl acetate). This gave the title compound (4.98 g, 6.89 mmol, 14%) as a pale-brown foam.

EXAMPLE 3

Photographic Evaluation

Controls were prepared by dispersing DIR coupler A3 in coupler solvent and incorporating it, together with the yellow image coupler Y-1 (also dispersed in coupler solvent), into photographic coatings containing a 1 μm magenta-sensitised tabular grain silver chloride (0.3% dump iodide) emulsion, on a cellulose acetate based support, according to the coating diagram shown in Format A.

Format A

| Gel Supercoat | |
| --- | --- |
| Gelatin | 1.00 g/m² |
| Emulsion Layer | |
| Silver chloride | 0.55 g/m² |
| Image coupler Y-1 | 1.80 mmol/m² |
| DIR Coupler A3 | X mmol/m² |
| Gelatin | 2.42 g/m² |
| Bis(vinylsulfonyl)methane (hardener) | 0.069 g/m² |
| Cellulose Acetate Support (with Gel U-coat and removable carbon antihalation backing) | | where X = 0, 0.022, 0.108, 0.216 mmol/m².

where X=0, 0.022, 0.108, 0.216 mmol/m².

In this way controls were prepared which contained no DIR or low percentages (1.2%, 5.7% and 10.7%) of DIR coupler A3 relative to the total amount of coupler (on a molar basis).

Aqueous dispersions of the couplers were prepared by methods known in the art.

The yellow image coupler (Y-1) dispersion contained 6% by weight of gelatin, 9% by weight of coupler and a 1.0:0.5:1.5 weight ratio of coupler to di-n-butyl phthalate coupler solvent to cyclohexanone auxiliary solvent. The auxiliary solvent was included to aid in dispersion preparation and was removed by washing the dispersion for 6 h at 4C and pH 6.0.

The yellow DIR coupler A3 dispersion contained 6% by weight of gelatin, 1% by weight of coupler and a 1.0:1.0:2.0 weight ratio of coupler to di-n-butyl phthalate coupler solvent to cyclohexanone auxiliary solvent. The auxiliary solvent was included to aid in dispersion preparation and was removed by washing the dispersion for 6 h at 4C and pH 6.0.

Photographic elements of the invention and comparative examples were prepared by dispersing the appropriate DIR coupler in coupler solvent and incorporating it, together with the yellow image coupler Y-1 (also dispersed in coupler solvent), into photographic coatings containing a 1 μm magenta-sensitised tabular grain silver chloride (0.3% dump iodide) emulsion, on a cellulose acetate based support, according to the coating diagram shown in Format B.

Format B

| Gel Supercoat | |
| --- | --- |
| Gelatin | 1.00 g/m² |
| Emulsion Layer | |
| Silver chloride | 0.55 g/m² |
| Image coupler Y-1 | 1.80 − X mmol/m² |
| DIR Coupler | X mmol/m² |
| Gelatin | 2.42 g/m² |
| Bis(vinylsulfonyl)methane (hardener) | 0.069 g/m² |
| Cellulose Acetate Support (with Gel U-coat and removable carbon antihalation backing) | | where X = 0, 0.045, 0.90, 1.35 mmol/m².

where X=0, 0.45, 0.90 and 1.35 mmol/m².

In this way photographic elements were prepared which contained no DIR or high percentages (25%, 50% and 75%) of DIR coupler relative to the total amount of coupler (on a molar basis).

Aqueous dispersions of the couplers were prepared by methods known in the art.

Both the yellow image coupler (Y-1) dispersion and the DIR coupler dispersions contained 6% by weight of gelatin, 9% by weight of coupler and a 1.0:0.5:1.5 weight ratio of coupler to di-n-butyl phthalate coupler solvent to cyclohexanone auxiliary solvent. The auxiliary solvent was included to aid in dispersion preparation and was removed by washing the dispersion for 6 h at 4C and pH 6.0.

Sensitometric Testing

The experimental photographic coatings prepared according to both Format A and Format B as described above were slit and chopped into 30 cm×35mm test strips. After hardening the strips were exposed (0.1 s) through a 0–4.0 neutral density step wedge (0.2 ND step increments) and Daylight V and Wratten 9 filters then processed through a standard C-41 process as described in the British Journal of Photography Annual (1988) 196–198 using the following steps and process times:

| Developer | 1.5 minutes |
| --- | --- |
| Stopbath | 1.0 minute |
| Wash | 2.0 minutes |
| Bleach | 4.0 minutes |
| Wash | 2.0 minutes |
| Fix | 4.0 minutes |
| Wash | 2.0 minutes |

(N.B. The stopbath is prepared by adding glacial acetic acid to demin. water until pH 3.0 is achieved.)

For each test strip, Status M densities were measured as a function of exposure using a spectral array automatic transmission densitometer. Measurements of sensitometric parameters—maximum density ($D_{max}$) and contrast (γ)—were obtained from plots of density vs. log exposure (DlogE curves).

In addition silver development effects were investigated by exposing a set of strips prepared as above for 0.01 sec through a 0–1.8 neutral density step wedge (0.3 ND increments) and Daylight V and Wratten 9 filters and processing through a modified C-41 process, in which the bleach step was omitted and a stopbath (1% acetic acid solution) was inserted after the developer step, using the following processing sequence:

| | |
|---|---|
| Developer | 1.5 minutes |
| Stopbath | 1.0 minute |
| Wash | 2.0 minutes |
| Fix | 4.0 minutes |
| Wash | 2.0 minutes |

The strips processed through the "no bleach" process were subjected to XRF analysis to determine the amount of developed silver in each of the seven steps of the processed strip. Silver development curves (developed silver in mg/m$^2$ vs. step number (or log exposure)) were then created. Visual inspection of the silver development curves was used to assess any silver inhibition effects exhibited.

The DlogE curves for the low % (Format A) and high % (Format B) incorporation series of DIR coupler A3 with the yellow image coupler Y-1 are displayed in FIG. 1. The effect of incorporation of the DIR coupler A3 and the comparative example CY-1 on contrast ($\gamma$) and maximum density ($D_{max}$) is shown in Table 1.

TABLE 1

| | Format | DIR Coupler | % DIR in Total Coupler | $\gamma$ Change (%) | Dmax Change (%) |
|---|---|---|---|---|---|
| Control | A | A3 | 1.2 | −29.7 | +4.9 |
| Control | A | A3 | 5.7 | −32.8 | −0.5 |
| Control | A | A3 | 10.7 | −38.4 | −6.9 |
| Comparative | B | CY-1 | 25 | −44.4 | −11.1 |
| Comparative | B | CY-1 | 50 | −47.1 | −24.0 |
| Comparative | B | CY-1 | 75 | −52.9 | −40.9 |
| Invention | B | A3 | 25 | −56.5 | −29.4 |
| Invention | B | A3 | 50 | −67.7 | −42.2 |
| Invention | B | A3 | 75 | −74.6 | −53.4 |

It can clearly be seen that at the high % DIR incorporations of the invention not only is a much higher reduction in contrast ($\gamma$) obtained but also a significant reduction in maximum density ($D_{max}$) is achieved compared with the controls having low % DIR incorporations. It can further be seen that there is considerably more reduction in contrast and $D_{max}$ with the DIR A3 used in the invention than is obtained by incorporating the comparative DIR CY-1.

Figure 2:
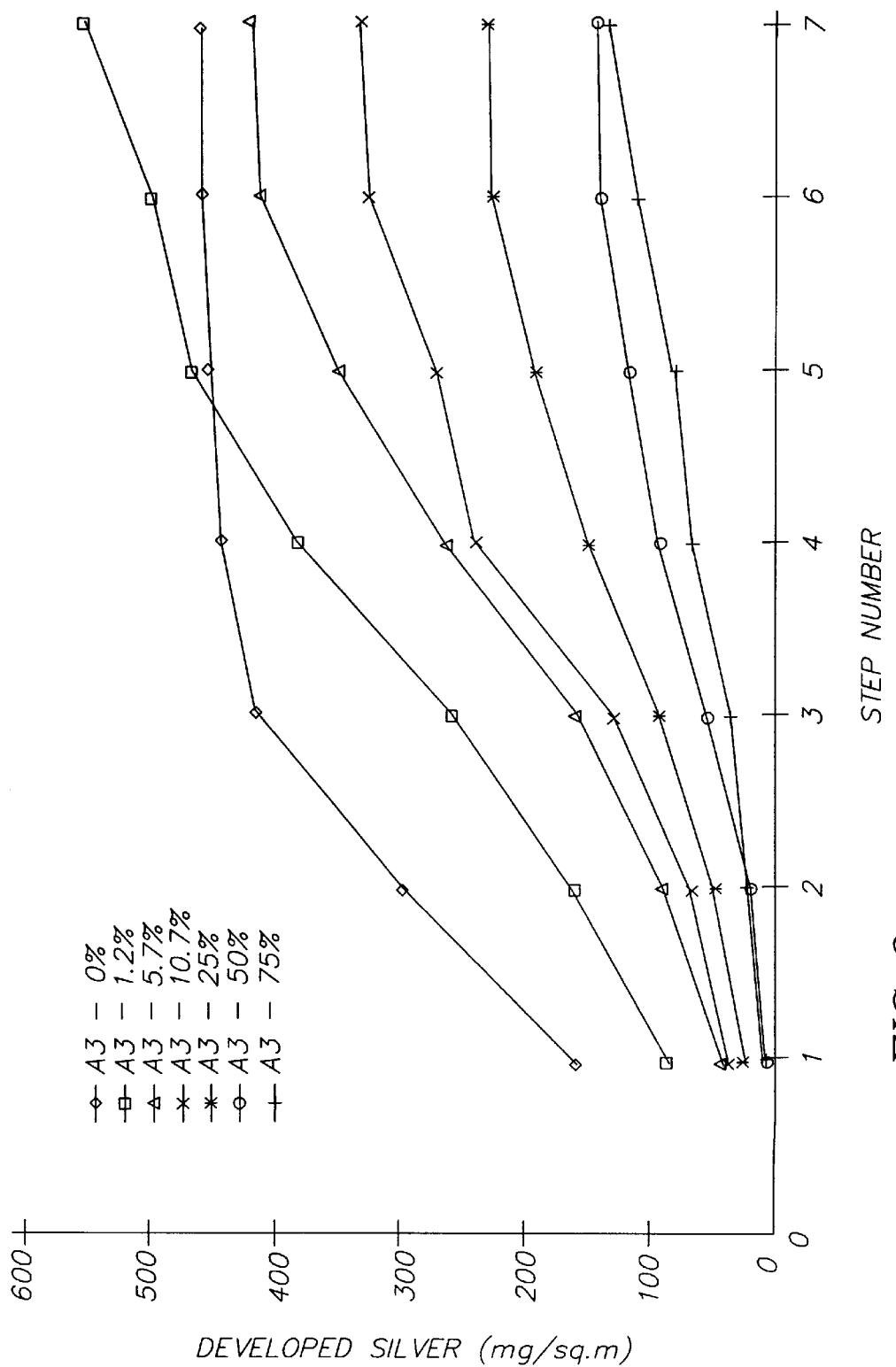
FIG. 2 shows corresponding plots of developed silver vs. log exposure or step number (silver development curves) for the series of FIG. 1.

The silver development curves for the image coupler Y-1/DIR coupler A3 combinations at low and high % DIR incorporations are shown in FIG. 2.

It is evident that the dye density profiles shown in FIG. 1 are a direct consequence of the inhibition of silver development shown in FIG. 2. The amount of inhibition (as measured by % reduction in silver developed at $D_{max}$) is shown in Table 2.

TABLE 2

| | Format | DIR Coupler | % DIR in Total Coupler | Change in Silver Development at Dmax (%) |
|---|---|---|---|---|
| Control | A | A3 | 1.2 | +20.9 |
| Control | A | A3 | 5.7 | −8.5 |
| Control | A | A3 | 10.7 | −28.0 |
| Comparative | B | CY-1 | 25 | +3.0 |
| Comparative | B | CY-1 | 50 | −22.6 |
| Comparative | B | CY-1 | 75 | −50.4 |
| Invention | B | A3 | 25 | −50.0 |
| Invention | B | A3 | 50 | −68.9 |
| Invention | B | A3 | 75 | −71.1 |

From Table 2 it can be seen that at the high % incorporations of the DIR A3 in the photographic elements of the invention a much larger inhibition of silver development is achieved than that obtained when the DIR A3 is incorporated at low % of total coupler (controls). It can further be seen that there is considerably more reduction in silver development with the DIR A3 used in the invention than is obtained by incorporating the comparative DIR CY-1.

EXAMPLE 4

Photographic Evaluation

Photographic elements of the invention and comparative examples were prepared by dispersing the appropriate DIR coupler in coupler solvent and incorporating it, together with the magenta image coupler M-1 (also dispersed in coupler solvent), into photographic coatings containing a 1 $\mu$m magenta-sensitised tabular grain silver chloride (0.3% dump iodide) emulsion, on a cellulose acetate based support, according to the coating diagram shown in Format C.

Format C

| | |
|---|---|
| Gel Supercoat | |
| Gelatin | 1.00 g/m$^2$ |
| Emulsion Layer | |
| Silver chloride | 0.55 g/m$^2$ |
| Image coupler M-1 | 0.90 − X mmol/m$^2$ |
| DIR Coupler | X mmol/m$^2$ |
| Gelatin | 2.42 g/m$^2$ |
| Bis(vinylsulfonyl)methane (hardener) | 0.069 g/m$^2$ |
| Cellulose Acetate Support (with Gel U-coat and removable carbon antihalation backing) | | where X = 0, 0.225, 0.45, 0.675 mmol/m$^2$.

where X=0, 0.225, 0.45 and 0.675 mmol/m$^2$

In this way photographic elements were prepared which contained no DIR or high percentages (25%, 50% and 75%) of DIR coupler relative to the total amount of coupler (on a molar basis).

Aqueous dispersions of the couplers were prepared by methods known in the art.

Both the magenta image coupler (M-1) dispersion and the DIR coupler dispersions contained 6% by weight of gelatin, 8.8% by weight of coupler and a 1.0:0.5:1.5 weight ratio of coupler to tricresyl phosphate coupler solvent to 2-(2-butoxyethoxy)ethyl acetate auxiliary solvent. The auxiliary solvent was included to aid in dispersion preparation and was removed by washing the dispersion for 6 h at 4C and pH 6.0.

Sensitometric Testing

The experimental photographic coatings prepared according to Format C as described above were slit and chopped into 30 cm×35 mm test strips. After hardening the strips were exposed and processed as described in Example 3 above.

Figure 3:
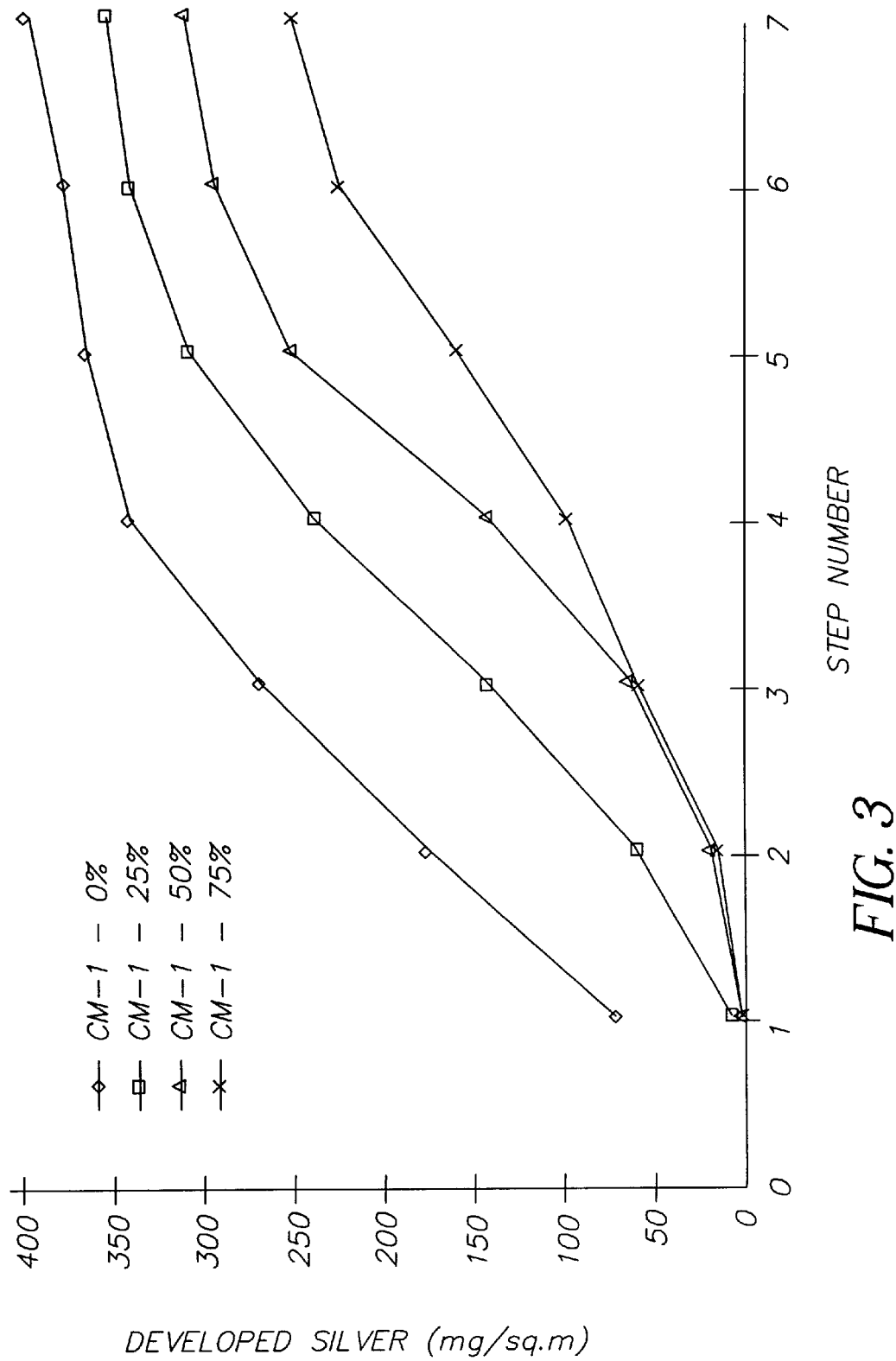
FIG. 3 shows silver development curves for a series of high percentage incorporations of a comparative magenta DIR coupler with a magenta image coupler.
Figure 4:
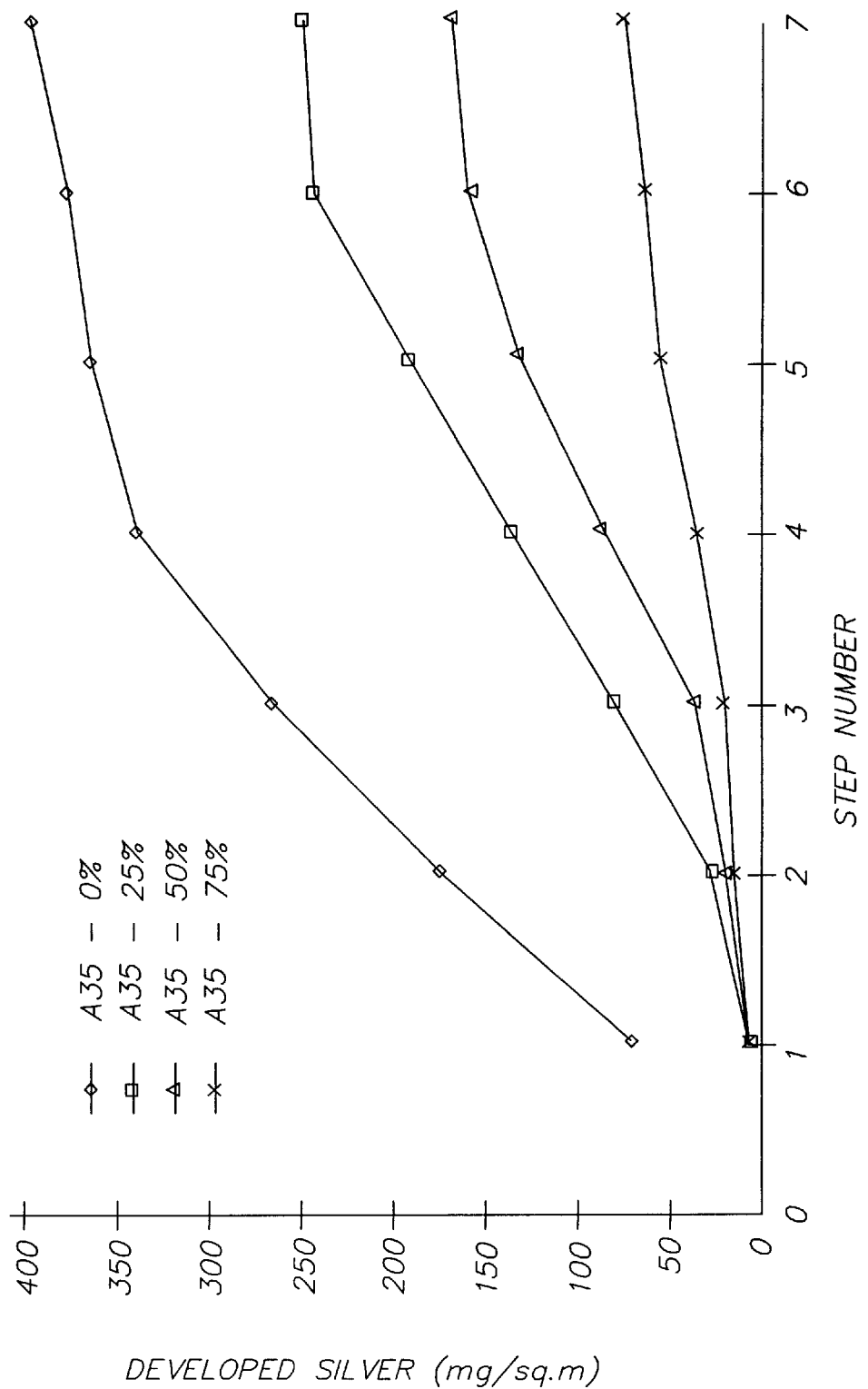
FIGS. 4 and 5 show corresponding silver development curves for a series of high percentage incorporations (the invention) of magenta DIRs with a magenta image coupler.
Figure 5:
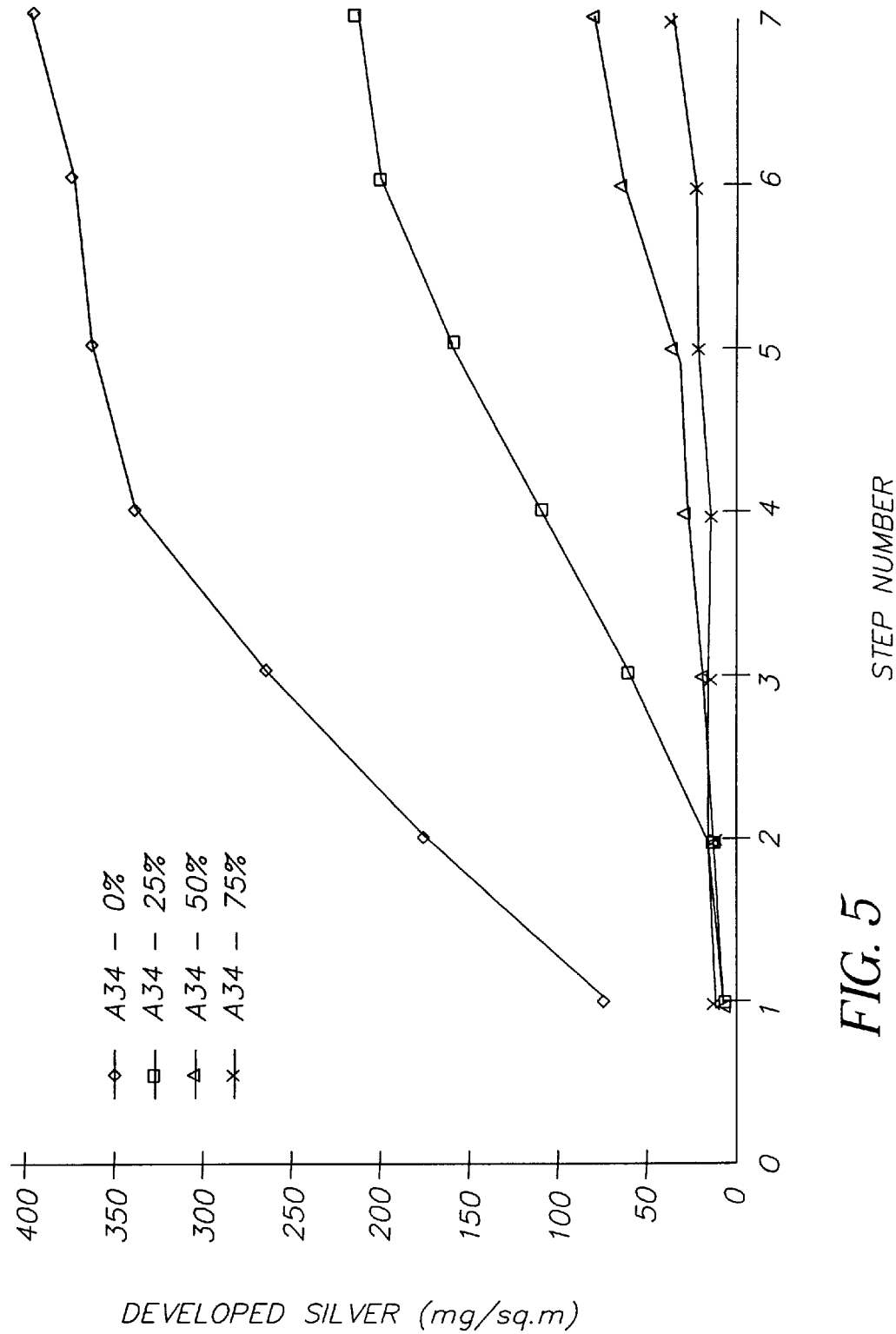

Silver development curves for the high % incorporation series of DIR couplers CM-1, A35 and A34 with the magenta image coupler M-1 are displayed in FIG. 3, FIG. 4 and FIG. 5 respectively.

The amount of inhibition (as measured by % reduction in silver developed at $D_{max}$) is shown in Table 3.

TABLE 3

| Format | DIR Coupler | % DIR in Total Coupler | Change in Silver Development at Dmax (%) |
| --- | --- | --- | --- |
| Comparative | C | CM-1 | 25 | −10.8 |
| Comparative | C | CM-1 | 50 | −21.9 |
| Comparative | C | CM-1 | 75 | −37.2 |
| Invention | C | A35 | 25 | −37.7 |
| Invention | C | A35 | 50 | −57.5 |
| Invention | C | A35 | 75 | −81.4 |
| Invention | C | A34 | 25 | −45.5 |
| Invention | C | A34 | 50 | −80.2 |
| Invention | C | A34 | 75 | −91.5 |

From Table 3 it can be seen that at the high % incorporations of the DIR A34 in the photographic elements of the invention a very high level of inhibition of silver development is achieved. The silver inhibition achieved with elements of the invention containing DIR A35 is only slightly less than that observed with the DIR A34. It can further be seen that there is considerably more reduction in silver development with the DIRs A34 and A35 used in the invention than is obtained by incorporating the comparative DIR CM-1.

What we claim is:

1. A photographic element comprising a support bearing one or more silver halide emulsions at least one of which comprises at least 50% silver chloride in association with one or more image dye-forming couplers and one or more DI(A)R couplers of formulae I or II:

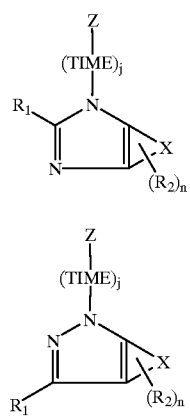

wherein:
   Z is a moiety which can react with oxidized developer to release a coupling-off group;
   $R_1$ is a hydrogen atom or a group selected from a halogen atom and an unsubstituted or substituted alkyl, aryl, alkoxy, aryloxy, alkyl- or aryl-thio, amino, alkyl- or aryl-amino, carbonamido, carbamoyl, alkoxy- or aryloxy-carbonyl, alkyl- or aryl-carbonyl, sulfonyl and sulfonamido group;
   each of the $R_2$ substituents is a halogen atom or a group selected from an unsubstituted or substituted alkyl, aryl, alkoxy, aryloxy, alkyl- or aryl-thio, amino, alkyl- or aryl-amino, carbonamido, carbamoyl, alkoxy- or aryloxy-carbonyl, alkyl- or aryl-carbonyl, sulfonyl and sulfonamido group;
   X represents the atoms required to make a second ring which is aromatic and contains at least one nitrogen atom;
   n is from 0 to the number of carbon atoms in the second ring, with the proviso that if $R_1$ is hydrogen, n is at least 1;
   TIME is a timing group and
   j is 0,1 or 2,
wherein the DI(A)R coupler comprises at least 30% to about 90% of the total amount of coupler and the total amount of coupler is the sum of the number of moles of image coupler and the number of moles of the DI(A)R coupler.

2. A photographic element as claimed in claim 1 wherein the DI(A)R coupler comprises at least 30% to about 80% of the total amount of coupler.

3. A photographic element as claimed in claim 2 wherein the DI(A)R coupler(s) comprises at least about 50% to about 75% of the total amount of coupler.

4. A photographic element as claimed in claim 1 wherein at least one of the silver halide emulsions comprises at least 70% silver chloride.

5. A photographic element as claimed in claim 4 wherein at least one of the silver halide emulsions comprises at least 90% silver chloride.

6. A photographic element as claimed in claim 1 wherein the silver chloride emulsion has T-grain morphology.

7. A photographic element as claimed in claim 1 wherein one or more DI(A)R couplers is of formulae III or IV:

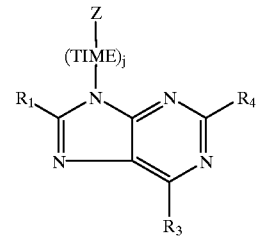

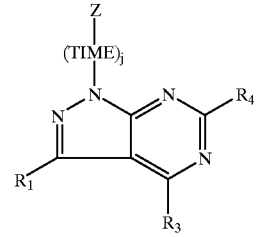

wherein:
   Z is a moiety which can react with oxidized developer to release a coupling-off group;
   $R_1$ is a hydrogen atom or a group selected from a halogen atom and an unsubstituted or substituted alkyl, aryl, alkoxy, aryloxy, alkyl- or aryl-thio, amino, alkyl- or aryl-amino, carbonamido, carbamoyl, alkoxy- or aryloxy-carbonyl, alkyl- or aryl-carbonyl, sulfonyl and sulfonamido group;

TIME is a timing group;

j is 0,1 or 2;

each of $R_3$ and $R_4$ is a hydrogen atom, a halogen atom or a group selected from an unsubstituted or substituted alkyl, aryl, alkoxy, aryloxy, alkyl- or aryl-thio, amino, alkyl- or aryl-amino, carbonamido, carbamoyl, alkoxy- or aryloxy-carbonyl, alkyl- or aryl-carbonyl, sulfonyl and sulfonamido group; with the proviso that at least one of $R_1$, $R_3$ and $R_4$ is not a hydrogen atom.

8. A photographic element as claimed in claim 7 wherein the combined sum of Hammett sigma para values for $R_1$, $R_3$ and $R_4$ is less than 1.0.

9. A photographic element as claimed in claim 1 wherein Z is selected from acylacetanilides, β-ketoketones, β-ketoesters, indanones, pyrazolones, pyrazoloazoles, phenols and naphthols.

10. A photographic element as claimed in claim 1 wherein j is 0.

11. A photographic element as claimed in claim 1 wherein one or more DIR couplers is of formulae V or VI:

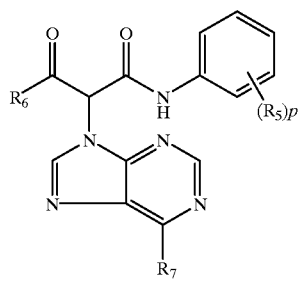

V

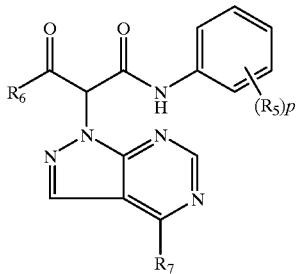

VI wherein:

each $R_5$ is a halogen atom, a cyano group or a group selected from an unsubstituted or substituted alkyl, aryl, alkoxy, aryloxy, acyloxy, alkyl- or aryl-thio, carbonamido, carbamoyl, alkoxy- or aryloxy-carbonyl, alkyl- or aryl-carbonyl, sulfonyl, sulfonamido, sulfoxyl, and sulfonate group;

$R_6$ is selected from the group consisting of an unsubstituted or substituted tertiary alkyl, aryl, heterocyclic and alkyl-and aryl-amino groups;

$R_7$ is a halogen atom or a group selected from an unsubstituted or substituted alkyl, aryl, alkoxy, aryloxy, alkyl- or aryl-thio, amino, alkyl- or aryl-amino, carbonamido, carbamoyl, alkoxy- or aryloxy-carbonyl, alkyl- or aryl-carbonyl, sulfonyl and sulfonamido group; and p is from 0 to 5.

12. A photographic element as claimed in claim 11 wherein one of the $R_5$ substituents is a halogen atom or an unsubstituted or substituted alkoxy group in the 2-position relative to the anilino nitrogen atom.

13. A photographic element as claimed in claim 11 wherein $R_6$ is an unsubstituted or substituted tertiary alkyl group or a phenyl group.

14. A photographic element as claimed in claim 11 wherein $R_7$ is an unsubstituted or substituted alkyl- or aryl-thio group, alkoxy or aryloxy group, alkyl -or aryl-amino group or a carbonamido group.

15. A photographic element as claimed in claim 11 having the structure:

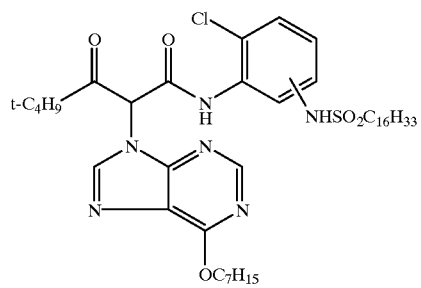

16. A photographic element as claimed in claim 1 wherein one or more DIR couplers is of formulae VII or VIII:

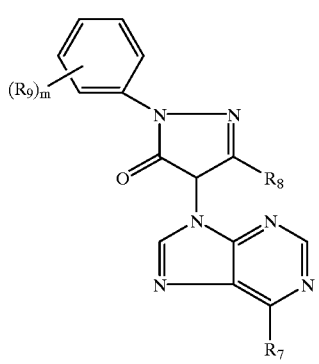

VII

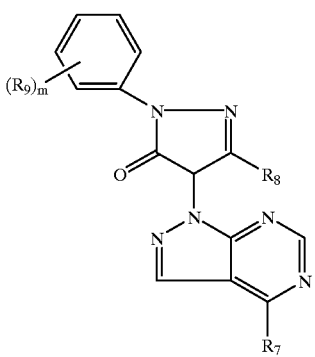

VIII wherein $R_7$ is a halogen atom or a group selected from an unsubstituted or substituted alkyl, aryl, alkoxy, aryloxy, alkyl- or aryl-thio, amino, alkyl- or aryl-amino, carbonamido, carbamoyl, alkoxy- or aryloxy-carbonyl, alkyl- or aryl-carbonyl, sulfonyl and sulfonamido group;

$R_8$ is an unsubstituted or substituted alkyl, aryl, alkyl- or aryl-amino or carbonamido group, $R_9$ is a halogen atom, a cyano group or a group selected from an unsubstituted or substituted alkyl, aryl, alkoxy, aryloxy, acyloxy, alkyl- or aryl-thio, carbonamido, carbamoyl, alkoxy- or aryloxy-carbonyl, alkyl- or aryl-carbonyl, sulfonyl, sulfonamido, sulfoxyl and sulfonate group; and m is from 0 to 5.

17. A photographic element comprising a support bearing one or more silver halide emulsions at least one of which comprises at least 50% silver chloride in association with one or more image dye-forming couplers and a DI(A)R coupler of formula:

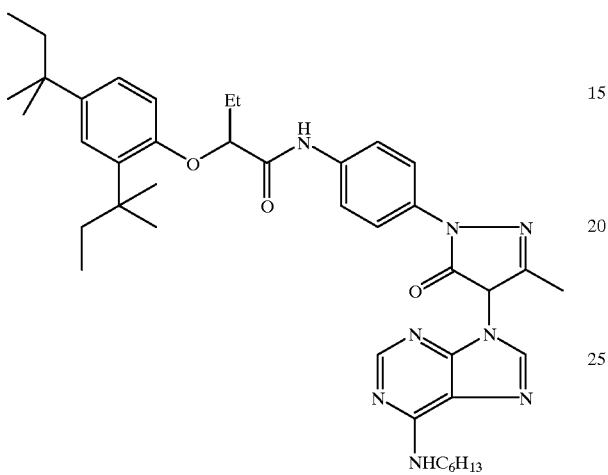

wherein the DI(A)R coupler comprises at least 30% to about 90% of the total amount of coupler and the total amount of coupler is the sum of the number of moles of image coupler and the number of moles of the DI(A)R coupler.

18. A photographic element comprising a support bearing one or more silver halide emulsions at least one of which comprises at least 50% silver chloride in association with one or more image dye-forming couplers and a DI(A)R coupler of formula:

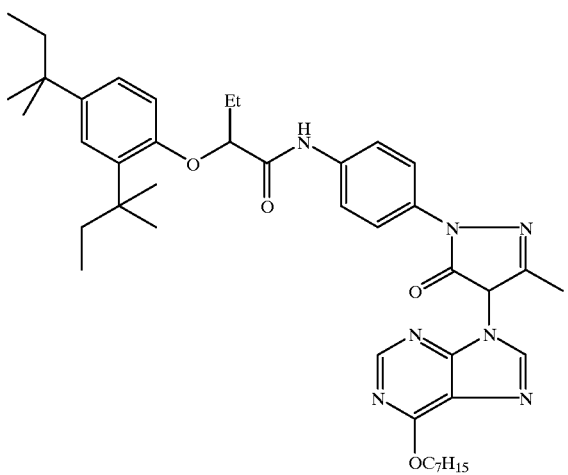

wherein the DI(A)R coupler comprises at least 30% to about 90% of the total amount of coupler and the total amount of coupler is the sum of the number of moles of image coupler and the number of moles of the DI(A)R coupler.

19. A multicolour photographic element comprising a support bearing a cyan image-dye-forming unit comprising a red-sensitive silver halide emulsion layer and a cyan dye-forming coupler; a magenta image-dye-forming unit comprising at least one green-sensitive silver halide emulsion layer and a magenta dye-forming coupler; a yellow image-dye-forming unit comprising at least one blue-sensitive silver halide layer and a yellow dye-forming coupler, and associated therewith at least one compound of general formula (I) or (II)

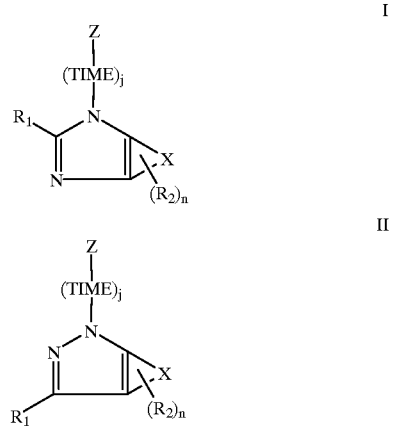

wherein:
Z is a moiety which can react with oxidized developer to release a coupling-off group;

$R_1$ is a hydrogen atom or a group selected from a halogen atom and an unsubstituted or substituted alkyl, aryl, alkoxy, aryloxy, alkyl- or aryl-thio, amino, alkyl- or aryl-amino, carbonamido, carbamoyl, alkoxy- or aryloxy-carbonyl, alkyl- or aryl-carbonyl, sulfonyl and sulfonamido group;

each of the $R_2$ substituents is a halogen atom or a group selected from an unsubstituted or substituted alkyl, aryl, alkoxy, aryloxy, alkyl- or aryl-thio, amino, alkyl- or aryl-amino, carbonamido, carbamoyl, alkoxy- or aryloxy-carbonyl, alkyl- or aryl-carbonyl, sulfonyl and sulfonamido group;

X represents the atoms required to make a second ring which is aromatic and contains at least one nitrogen atom;

n is from 0 to the number of carbon atoms in the second ring, with the proviso that if $R_1$ is hydrogen, n is at least 1;

TIME is a timing group and j is 0,1 or 2, wherein at least one of the layers comprises an emulsion comprising at least 50% silver chloride, and wherein in any one layer the DI(A)R coupler comprises at least 30% to about 90% of the total amount of coupler in that layer, wherein the total amount of coupler is the sum of the number of moles of image coupler and the number of moles of the DI(A)R coupler.

20. A multicolor photographic element as claimed in claim 19 wherein one or more DI(A)R couplers are in the layer comprising an emulsion comprising at least 50% silver chloride.

* * * * *